US006407313B1

(12) United States Patent
Lucas

(10) Patent No.: US 6,407,313 B1
(45) Date of Patent: *Jun. 18, 2002

(54) REGULATION OF PLANT DEVELOPMENT AND PHYSIOLOGY THROUGH PLASMODESMATAL MACROMOLECULAR TRANSPORT OF PROTEINS AND OLIGONUCLEOTIDES

(75) Inventor: William J. Lucas, Davis, CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/760,006

(22) Filed: Dec. 4, 1996

Related U.S. Application Data

(63) Continuation-in-part of application No. 08/698,461, filed on Aug. 15, 1996, now abandoned, which is a continuation-in-part of application No. 08/515,707, filed on Aug. 16, 1995, now abandoned.
(60) Provisional application No. 60/007,915, filed on Dec. 4, 1995.

(51) Int. Cl.[7] .............................................. C12N 15/82
(52) U.S. Cl. ........................ 800/280; 800/284; 800/290
(58) Field of Search ............................. 536/23.72, 23.6; 435/172.1, 172.3, 375, 69.1, 468, 419, 320.1, 440; 800/205, 298, 278

(56) References Cited

U.S. PATENT DOCUMENTS

| | | | |
|---|---|---|---|
| 5,159,135 A | 10/1992 | Umbeck ...................... 800/205 |
| 5,169,770 A | 12/1992 | Chee et al. ............... 435/172.3 |
| 5,177,010 A | 1/1993 | Goldman et al. ......... 435/172.3 |
| 5,187,073 A | 2/1993 | Goldman et al. ......... 435/172.3 |
| 5,188,958 A | 2/1993 | Moloney et al. .......... 435/240.4 |
| 5,215,912 A | 6/1993 | Hoffman ................... 435/240.4 |
| 5,262,306 A | 11/1993 | Robeson et al. ............... 435/29 |
| 5,262,316 A | 11/1993 | Engler et al. ................ 435/172 |
| 5,268,526 A | 12/1993 | Hershey et al. ............. 800/205 |
| 5,286,635 A | 2/1994 | Hanson et al. ............ 435/172.3 |
| 5,340,730 A | 8/1994 | Graves et al. ............. 438/172.3 |
| 5,364,780 A | 11/1994 | Hershey et al. .......... 435/172.3 |
| 5,376,543 A | 12/1994 | Chee et al. ............... 435/172.3 |

OTHER PUBLICATIONS

Xoconostle–Cazares, B. et al., "Plant Paralog to Viral Movement Protein That Potentiates Transport of mRNA into the Phloem." 1999, Science, vol. 283, pp. 94–98.*

Schwarz–Sommer, Z. et al., "Characterization of the Antirrhinum Floral Homeotic Mads–Box Gene Deficiens Evidence Evidence for DNA Binding and Autoregulation of its Persistent Expression throughout Flower Development." 1992, EMBO, J., vol. 11(1), pp. 251–264.*

Sinha, N. R. et al., "Overexpression of the maize homeo box gene, KNOTTED–1, causes a switch from determinate to indeterminate cell fates." 1993, Genes & Development, vol. 7 (5), pp. 787–795.*

Stam M, et al. "The silence of genes in transgenic plants." Ann. Bot. 79: 3–12, 1997.*

Koziel MG, et al. "Optimizing expression of transgenes with an emphasis on post–transcriptional events." Plant Mol. Biol. 32: 393–405, 1996.*

Smith CJS, et al. "Antisense RNA inhibition of polygalacturonase gene expression in transgenic tomatoes." Nature 334: 724–726, Aug. 25, 1988.*

Lucas WJ, et al. "Influence of modified plasmodesmata on carbon allocation in transgenic tobacco plants." Plant Physiol. 93: 119, 1990.*

Wolf S, et al. "Plasmodesmatal function is probed using transgenic tobacco plants that express a virus movement protein," Plant Cell 3: 593–604, 1991.*

Smith LG, et al. "Molecular approaches to leaf development: Knotted and beyond." Can. J. Bot. 72: 617–625, May 1994.*

Volbrecht E, et al. "The developmental gene Knotted–1 is a member of a maize homeobox gene family." Nature 350: 241–243, 1991.*

Epel BL. "Plasmodesmata: Composition, structure and trafficking." Plant Mol. Biol. 26: 1343–1356, 1994.*

*Science*, vol. 246, pp. 377–379, Oct. 1989, Movement Protein of Tobacco Mosaic Virus Modified Plasmodesmatal Size Exclusion Limit, S. Wolf, C.M. Deom, R.N. Beachy and W.J. Lucas.

*Plant Physiology*, 1986,82, pp. 423–442, Symplastic Transport in *Ipomeca tricolor* Sourse Leaves, M.M. Madore, J.W. Oross, W.J. Lucas.

2nd International Workshop, Oosterbeck, The Netherlands, September 1992, *Basic and Applied Research in Pladmodesmatal Biology*, Parallels Between Plasmodesmal and Nuclear Transport, C. van der Schoot, B. Ding and W. Lucas.

*The Plant Cell*, vol. 5, 1783–1794, Dec. 1993, Cell–to–Cell Trafficking of Macromolecules Through Plasmodesmata Potentiated by the Red Clover Necrotic Mosaic Virus Movement Protein, T. Fujiwara, D. Giesman–Cookmeyer, B. Ding, S.A. Lommel, W. Lucas.

(List continued on next page.)

Primary Examiner—Amy J. Nelson
(74) Attorney, Agent, or Firm—John P. O'Banion

(57) ABSTRACT

Methods and mechanisms for regulation of macromolecular transport between cells in plasmodesmatal communication with one another are disclosed. Nuclear acids encoding tobacco mosaic virus movement protein (TMV-MP) in wild type and mutant forms is shown and used to affect plant size, carbon metabolism and biomass partitioning in transgeric plants.

18 Claims, 7 Drawing Sheets

OTHER PUBLICATIONS

Figure 1A:
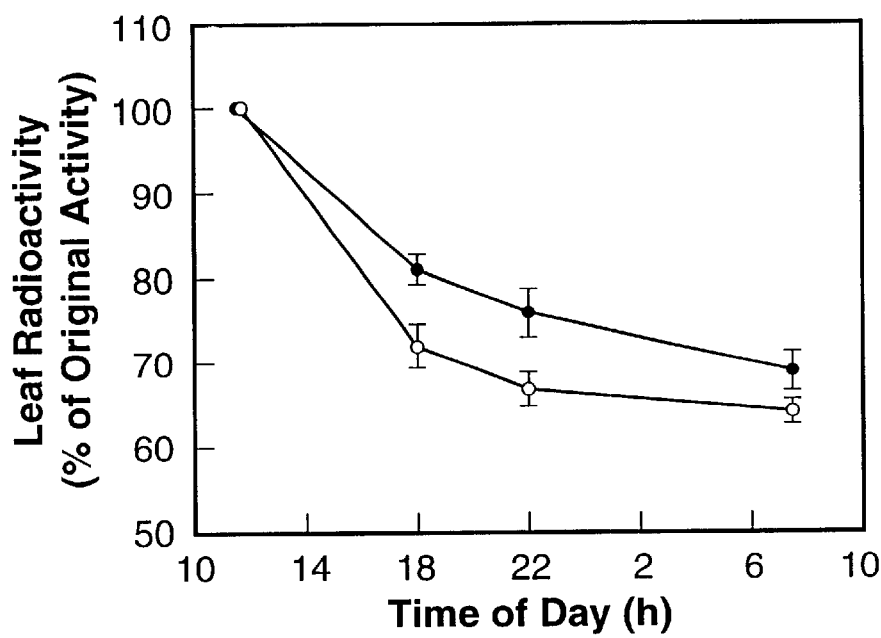

*The Plant Journal*, 1993, 4(1), 179–189, Correlation between arrested secondary plasmodesmal development and onset of acceleration leaf senescence in yeast acid invertase transgenic tobacco plants, B. Ding, J.S. Haudenshield, L. Willmitzer, W.J. Lucas.

*Planta* 1993, 190: 88–96, Influence of the tobacco mosaic virus 30–kDa movement protein on carbon metabolism and photosynthate partitioning in transgenic tobacco plants, W.J. Lucas, A. Olesinski, R. J. Hull, J.S. Haudenshield, C.M. Deom, R.N. Beachy, S. Wolf.

*Cell*, vol. 76, No. 5, pp. 925–932, Mar. 1994, Two Proteins of a Plant DNA Virus Coordinate Nuclear and Plasmodesmal Transport, A.O. Noueiry, W.J. Lucas, R.L. Gilbertson.

*Current Opinions in Cell Biology* 1995, 7:673–680, Plasmodesmata: intercellular channels for macromolecular transport in plants, W.J. Lucas.

*Plant, Cell and Env.*, Jun. 1995 (unconfirmed), Alteration in carbon partitioning, induced by the movement protein of tobacco mosaic virus, originates from the mesophyll and is independent of change in plasmodesmalsize exclusion limit (Running Title: TMV–MP alters biomass partitioning in transgenic tobacco) S. Balachandran,R.J. Hull, Y. Vaadia, S. Wolf, W.J. Lucas.

*Trends in Cell Biology*, vol. 3., pp. 308–315, Sep. 1993, Plasmodesmata: the intercellular organelles of green plants, W.J. Lucas, S. Wolf.

*Proc. Natl. Acad. Sci. USA*, vol. 91, pp. 1433–1437, Feb. 1994, Cell Biology, Direct Functional Assay for Tobacco Mosaic Virus Cell–to–Cell Movement Protein and Indentification of a Domain Involved in Increasing Plasmodesmal Permeability, E. Waigmann, W.J. Lucas, V. Citovsky, P. Sambryski.

*Annu. Rev. Plant Physiol. Plant. Mol. Biol.*, 1990, 41:369–419, Plasmodesmata, A.W. Robards, W.J. Lucas.

*New Phytol.*, 1993, 125, 435–476, Tansley Review No. 58 Plasmodesmata and the Supracellular Nature of Plants, W.J. Lucas, B. Ding, C. van der Schoot.

*Annu. Rev. Phytopathol.*, 1994, 32:387–411, Plasmodesmata in Relation to Viral Movement Within Leaf Tissues, W.J. Lucas, R.L. Gilbertson.

*Planta*, 1995, 196:205–210, Sieve–tube exudate from *Ricinus communisL.* seedlings contains ubiquitin and charperones. C. Schobert, P. Grobmann, M. Gottschalk, E. Komor, A. Pecsvaradi, U. zur Nieden.

*Plant Cell Physiol.*, 34(6): 927–933, 1993, Protein Phosphorylation in the Sieve Tubes of Rice Plants, S. Nakamura, H. Hayashi, S. Mori, M. Chino.

*Planta*, 1995, 195:456–463, Thioredoxin h is one of the major proteins in rice phloem sap, Y. Ishiwatari, C. Honda, I. Kawashim, S. Nakamure, H. Hirano, S. Mori, T. Fujiwara, H. Hayashi, M. Chino.

*Planta*, vol. 197 No. 1, 1995, pp. 118–126, Pleiotropic effects of tobacco–mosaic–virus movement protein on carbon metabolism in transgenic tobacco plants, A.A. Oleskini, W.J. Lucas, E. Galun, S. Wolf.

*Internatinal Conference on the Transport of Photoassimilates*, Aug. 13–17, 1995, Abstract: Plasmodesmata, macromolecular trafficking and the control over carbon partitioning in higher plants, W.J. Lucas, S. Balachandran, S. Wolf, A.A. Olesinski.

*Science*, Nov. 1996 (unconfirmed), Selective trafficking of KNOTTED1 homeodomain protein and its mRNA through plasmodesmata, W.J. Lucas, S. Bouche–Pillon, D.P. Jackson, L. Nguyen, L. Baker, B. Ding, S. Hake.

*Plant Molec. Bio.*, Nov. 1996 (unconfirmed), Plasmodesmal cell–to–cell transport of proteins and nucleic acids, L.A. Mezitt, W.J. Lucas.

*Journal of Experimental Botany*, vol. 47. Special Issue, pp. 000–000, Jul. 1996, Plasmodesmal companion cell–mesophyll communication in the control over carbon metabolism and phloem transport: insights gained from viral movement proteins, W.J. Lucas, S. Balachandran, J. Park, S. Wolf.

* cited by examiner

```
                                                              ┌──────────────┐      ┌──────────────┐
                                                          T→  │   Carbon     │ ───→ │  Decrease in │
                                                         ┌──→ │  Allocation  │      │ root-to-shoot│
                                                         │    └──────────────┘      │    ratio     │
┌──────────────┐    ┌──────────────┐    ┌──────────────┐ │                          └──────────────┘
│  TMV-MP      │    │  TMV-MP      │    │              │ │    ┌──────────────┐              ▲
│ increases in │───→│ endogenous   │───→│  Changes In  │─┼──→ │    Sugar     │              │
│ source leaf  │    │   protein    │    │              │ │    │  Metabolism  │─┐            │
│   cytosol    │    │ interactions │    │              │ │    └──────────────┘ │            │
└──────────────┘    │  (signals or │    └──────────────┘ │                     │            │
       ▲            │   enzymes)   │           ▲         │                     ▼            │
       │            └──────────────┘           │         │    ┌──────────────┐ ┌──────────┐ │
┌──────────────┐            ▲           T→     │         │    │    Starch    │ │Adjustments│
│ Constitutive │            │                  │         └──→ │  Metabolism  │→│in carbohyd.│
│ expression of│    ┌──────────────┐           │              └──────────────┘ │storage and │
│   TMV-MP in  │    │ Alteration in│    ┌──────────────┐             T→        │  export   │
│  transgenic  │───→│ endogenous PD│───→│  Shift in    │                       └──────────┘
│   tobacco    │    │macromolecular│    │  regulatory  │
│    plants    │    │  trafficking │    │   signals    │
└──────────────┘    └──────────────┘    │  controlling │
       │                                │  source leaf │
       │                                │   function   │
       ▼                                └──────────────┘
┌──────────────┐    ┌──────────────┐    ┌──────────────┐
│   TMV-MP     │    │   TMV-MP     │    │   TMV-MP     │
│  targets to  │───→│  Induced     │───→│  mediated    │
│ secondary PD │    │  increase in │    │   TMV RNA    │
│              │    │    PD SEL    │    │ PD trafficking│
└──────────────┘    └──────────────┘    └──────────────┘
```

FIG. – 3

```
                            M1                              50
MEEITQHFGVGASSHGHGHGQHHH HH HHHHPWASSLSAVVAPLPPQPPSA
                        |_____|
                             M2Δ
                                                           100
GLPLTLNTVAATGNSGGSGNPVLQLANGGGLLDACVKAKEPSSSSPYAGD

150
VEAIKAKIISHPHYYSLLTAYLECNKVGAPPEVSARLTEIAQEVEARQRT

M3                                         200
ALGGLAAATEP E L D QFMEAYHEMLVKFREELTRPLQEAMEFMRRVESQLN

M4                              M5           250
SLSISGRSLRNILSSGSS EED QEGSGGETELPEVDAHGVDQ E L K HHLLKK

M6      M7                                300
YSGYLSSLKQELSK KKK KGKLP KE ARQQLLSWWDQHYKWPYPSETQKVAL

M8       M9                                 350
AESTGLDLKQINNWFINQR KR HWKPS EE M HH LMMDGYHTTNAFYMDGHFI

359
NDGGLYRLG
```

Fig. 4. KN1 alanine scanning and deletion mutants generated to identify protein domain(s) essential for KN1-plasmodesmal interaction. (Conventional single-letter amino acid codes are used here for simplicity. See SEQ ID NO:1 for corresponding three-letter amino acid codes.) Amino acid residues changed to alanines are marked with black boxes, with the assigned number of each mutant indicated above the site. Deletion mutant M2 was generated by the removal of a 9 histidine stretch from position 22 to 30. The residues associated with the KN1 homeodomain are underlined. The domains affected by these mutations are as follows: M1 and M2, histidine-rich region of unknown function; M3 and M4, regions conserved between certain kn1 related genes; M5, the "ELK" region which is conserved in all KN1-like homeodomain proteins; M6, potential nuclear localization sequence; M7, homeodomain 1st helix; M8, homeodomain 3rd helix; M9, C-terminal border of homeodomain.

REGULATION OF PLANT DEVELOPMENT AND PHYSIOLOGY THROUGH PLASMODESMATAL MACROMOLECULAR TRANSPORT OF PROTEINS AND OLIGONUCLEOTIDES

CROSS REFERENCE TO RELATED APPLICATION

This is a Continuation-In-Part of application Ser. No. 08/698,461 filed Aug. 15, 1996, now abandoned, which is a continuation-in-art of U.S. application Ser. No. 08/515/707 filed Aug. 16, 1995, now abandoned. This application also claims priority from U.S. Provisional Application No. 60/007,915 filed Dec. 4, 1995, and from PCT Application Ser. No. PCT/US96/13299 filed on Aug. 15, 1996.

BACKGROUND OF THE INVENTION

1. Field of the Invention

The present invention relates generally to the field of plant biology. More particularly, the present invention is directed to compositions and methods for use in regulation of plant growth.

This invention was made with Government support under Grant No. DCB-90-16756 and INB-94-06974, awarded by the National Science Foundation, and Grant No. 90-00070, awarded by the United States Department of Agriculture. The Government has certain rights in this invention.

2. Description of the Related Art

Present strategies for controlling plant developmental and physiological functions rely on traditional genetic approaches, or on biotechnological approaches that lack a fully refined conceptual foundation. In terms of manipulation of plant resource allocation, the only approach currently available involves the use of genetic breeding for a desired trait; this is recognized as a slow and complex process. Furthermore, current strategies fail to provide any understanding of the underlying molecular events that are involved in the prioritization of resource allocation to the various regions of the plant body.

Partitioning of assimilates in plants is an important and highly regulated process [Wardlaw I. F. (1990) The control of carbon partitioning in plants. *New Phytologist* 116, 341–381]. It involves regulation of photosynthesis, intracellular and intercellular transport of metabolites, phloem loading and unloading, storage and other interrelated biochemical processes. Partition of assimilates is closely related to the regulation of growth and development, in as much as growth of different plant parts and organs often requires the import of assimilates from elsewhere in the plant. The relationship between root and shoot biomass is an excellent example of regulation of partition of assimilates. Root-to-shoot ratios vary from plant species-to-species, and are influenced by the environment [Geiger D. R. & Servaites J. S. (1991) Carbon allocation and response to stress. In *Response of plants to multiple stresses* (eds. H. A. Mooney, W. E. Winner & E. J. Pell) pp. 103–127. Academic Press, New York; Mooney H. A. & Winner W. E. (1991) Partitioning response of plants to stress. In *Response of plants to multiple stresses* (eds. H. A. Mooney, W. E. Winner & E. J. Pell) pp. 129–141. Academic Press, New York]. Furthermore, this ratio is responsive to water stress and nutrient deficiencies, and it can be manipulated by exogenous hormonal treatments and light quality [Britz S. J. (1990) Photoregulation of root: shoot ratio in soybean seedlings. *Photochemistry and Photobiology* 52, 151–159; Incoll L. D., Ray J. P. & Jewer P. C. (1990) Do cytokinins act as root to shoot signals? In *Importance of root to shoot communication in the responses to environmental stress*, Monograph 21 (eds. W. J. Davies & B. Jeffcoat) pp. 185–199. British Society for Plant Growth Regulation, Bristol; Davies W. J. & Zhang J. (1991) Root signals and the regulation of growth and development of plants in drying soil. *Annual Review of Plant Physiology and Plant Molecular Biology* 42, 55–76; Tolley-Henry L. & Raper C. D. (1991) Soluble carbohydrate allocation to roots, photosynthetic rate of leaves and nitrate assimilation as affected by nitrogen stress and irradiance. *Botanical Gazette* 152, 23–33].

The finding [Lucas W. J., Olesinski A., Hull R. J., Haudenshield J. S., Deom C. M., Beachy R. N. & Wolf S. (1993) Influence of the tobacco mosaic virus 30-kDa movement protein on carbon metabolism and photosynthate partitioning in transgenic tobacco plants. *Planta* 190, 88–96] that a significant reduction in biomass partitioning to roots occurs in transgenic tobacco plants that express the tobacco mosaic virus movement protein (TMV-MP) has raised questions as to the possible effects of this protein on the integrated physiology of tobacco plants. It is now well established that the TMV-MP interacts with plasmodesmata to potentiate virus trafficking between cells [Deom C. M., Oliver M. J. & Beachy R. N. (1987) The 30-kDa gene product of tobacco mosaic virus potentiates virus movement. *Science* 237, 389–394; Wolf S., Deom C. M., Beachy R. N. & Lucas W. J. (1989) Movement protein of tobacco mosaic virus modifies plasmodesmatal size exclusion limit. *Science* 246, 377–379; Ding B., Haudenshield J. S., Hull R. J., Wolf S., Beachy. R. N. & Lucas W. J. (1992) Secondary plasmodesmata are specific sites of localization of the tobacco mosaic virus movement protein in transgenic tobacco plants. *Plant Cell* 4, 915–928; Waigmann E., Lucas W. J., Citovsky V. & Zambryski P. (1994) Direct functional assay for tobacco mosaic virus cell-to-cell movement protein and identification of a domain involved in increasing plasmodesmal permeability. *Proc. Natl. Acad. Sci. USA* 91, 1433–1437]. In transgenic tobacco plants expressing the TMV-MP, the size exclusion limit (SEL) of plasmodesmata connecting the mesophyll and bundle sheath cells was found to be increased from 800 Da to greater than 9.4 kDa [Wolf et al. 1989, supra; Deom C. M., Wolf S., Holt C. A., Lucas W. J. & Beachy R. N. (1991) Altered function of the tobacco mosaic virus movement protein in a hypersensitive host. *Virology* 180, 251–256; Ding et al. 1992, supra]. This observation raised the possibility that dilated plasmodesmata, within such tissues, may enhance symplasmic carbohydrate transport between cells [Lucas W. J. & Wolf S. (1990) Plasmodesmatal function probed using transgenic tobacco plants. In *Recent advances in Phloem transport and assimilate compartmentation* (eds. J. L. Bonnemain, J. Dainty, S. Delrot & W. J. Lucas) pp. 106–115. Ouest Editions, Nantes Cedex; Lucas et al. 1993, supra]. However, contrary to this expectation, these transgenic plants exhibited a decrease in translocation of assimilates, from source leaves, during the day [Lucas et al. 1993, supra].

Also, in such transgenic plants expressing the TMV-MP, root-to-shoot ratios were significantly smaller, reflecting reduced carbon allocation and translocation to the roots [Lucas et al. 1993, supra]. It is thus of great interest that the TMV-MP affects not only the dilation of plasmodesmata and virus trafficking, but also carbohydrate metabolism and resource allocation, as reflected by changes in root-to-shoot ratios.

Similar considerations are involved in understanding the distribution of other plant products, such as sucrose. Sucrose synthesis occurs within the cytosol of tobacco mesophyll cells, but the pathway followed by sucrose during its movement from the site of synthesis to the cells of the phloem remains equivocal. The prevailing view is that solute movement between mesophyll cells occurs via a symplasmic route through plasmodesmata [Giaquinta, R. T. (1983) Phloem loading of sucrose. *Ann. Rev. Plant PhysioL* 34, 347–387; Tucker, J. E., Mauzerall, D., Tucker, E. B. (1989) Symplastic transport of carbxyfluorescin in staminal hairs of *Setcreasea purpurea* is diffusive and includes loss to the vacuole. *Plant Physiol.* 90, 1143–1147; Robards, A. W., Lucas, W. J. (1990) Plasmodesmata. *Annu. Rev. Plant PhysioL Plant Mol. Biol.* 41, 369–419]. In many species, however, the actual process involved in loading into the sieve element-companion cell complex may involve an apoplasmic step [van Bel, A. J. E. (1992) Pathway and mechanisms of phloem loading. In: *Carbon partitioning within and between organisms* (eds. Pollock, C. J., Farrar, J. F., Gordon, A. J.) pp. 53–70. BIOS Scientific Publishers, Ltd., Oxford]. Furthermore, it remains to be elucidated whether the loading process constitutes the rate-determining step, or major control site, in the export of recently fixed photosynthate.

Experimental control over plasmodesmal SEL has recently been achieved using expression of viral movement proteins (MPs) in transgenic plants. In transgenic tobacco expressing the MP of tobacco mosaic virus (TMV-MP), this movement protein becomes localized to mesophyll plasmodesmata [Atkins, D., Hull, R., Wells, B., Roberts, K., Moore, P., Beachy, R. N. (1991) The tobacco mosaic virus 30K movement protein in transgenic tobacco plants is localized to plasmodesmata. *J. Gen. Virol.* 72, 209–211; Ding et al. 1992, supra; Moore, P. J., Fenczik, C. A., Deom, C. M., Beachy, R. N. (1992) Developmental changes in plasmodesmata in transgenic tobacco expressing the movement protein of tobacco mosaic virus. *Protoplasma* 170, 115–127] where it causes a significant increase in plasmodesmal SEL from the control value of approx. 800 Da to greater than 9.4 kDa [Wolf et al. 1989, supra]. Photosynthesis and carbon allocation experiments performed on these transgenic tobacco plants revealed that the presence of the TMV-MP resulted in a change in carbon metabolism [Lucas et al. 1993, supra]. Although total chlorophyll, net photosynthesis and total leaf proteins were not significantly different between control and TMV-MP plant lines, it was found that, compared with control plants, fully expanded leaves expressing the TMV-MP had unexpectedly high levels of sugars and starch. The level of carbohydrates within these TMV-MP leaves appeared to increase more rapidly during the photoperiod, compared with control leaves, with the converse occurring during the dark period. In addition, there was a significant difference in biomass distribution between the various plant organs, resulting in lower root-to-shoot ratios in TMV-MP transgenic plants, although, under the growth conditions employed in these studies, the total biomass remained similar in both plant lines [Lucas et al. 1993, supra]. This complex influence of the TMV-MP on carbon metabolism was unexpected, since it was anticipated that increasing the plasmodesmal SEL would enhance symplasmic transport of sugars from the mesophyll to the site of phloem loading. If this were the case, sugar levels within the mesophyll tissue of TMV-MP plants should have been lower, not higher, than control values. Furthermore, if plasmodesmal SEL within the mesophyll did not constitute a rate-limiting step on the process of loading, carbon metabolism should have remained unaffected by the TMV-MP. Interpretation of these results was further complicated by the finding that although the TMV-MP was expressed in the vascular tissue, it did not cause an increase in the SEL of the plasmodesmata that interconnect the cells within the vein [Ding et al. 1992, supra].

It is an object of the present invention to provide compositions and methods which do not suffer from all of the drawbacks of the heretofore known compositions and methods.

SUMMARY OF THE INVENTION

In accordance with the present invention, there are provided methods and compositions for use in regulating plant metabolism and growth, wherein a plant regulatory composition (as hereinafter defined) is administered in a manner such that plasmodesmal transport of the composition in a predetermined manner is effected. Evidence is provided herein that plant encoded genes have the capacity to traffic via plasmodesmata to influence cell fate. In one example, TMV-MP is shown to interfere with an endogenous signal transduction pathway that involves macromolecular trafficking through plasmodesmata to regulate biomass partitioning between the source and various sink tissues. In another example, three homeotic proteins encoded by the maize homeobox gene Knotted-1and the MADS box genes deficiens and globosa of Antirrhinum [Sommer H., Nacken W., Beltran P., Huijser P., Pape H., Hansen R., Flor P., Saedler H., Schwartz-Sommer Z. (1991) Properties of deficiens, a homeotic gene involved in the control of flower morphogenesis in *Antirrhinum majus. Development Supp* 1, 169–175; Troebner W., Ramirez L., Motte P., Hue I., Huijser P., Loennig W.-E., Saedler H., Sommer H., Schwartz-Sommer Z. (1992) *GLOBOSA*: A homeotic gene which interacts with DEFICIENS in the control of Antirrhinum floral organogenesis. *EMBO J.* 11, 4693–4704] have now been shown to interact with plasmodesmata to mediate in their cell-to-cell transport. In yet another example, the first direct experimental proof that a plant mRNA-encoded protein can mediate in the plasmodesmal transport of itself and its own mRNA such that the mRNA can undergo extensive cell-to-cell movement is provided.

A further example illustrates that plant growth response to light intensity is altered by a viral movement protein. And in yet a different example, selective cell-to-cell movements of proteins through plasmodesmata are shown to potentiate cellular interactions between cells in adjacent cell layers, such as between layers of meristematic tissue and; between vascular tissue cells and cells in adjacent mesophyll and epidermal layers.

BRIEF DESCRIPTION

Figure 1B:
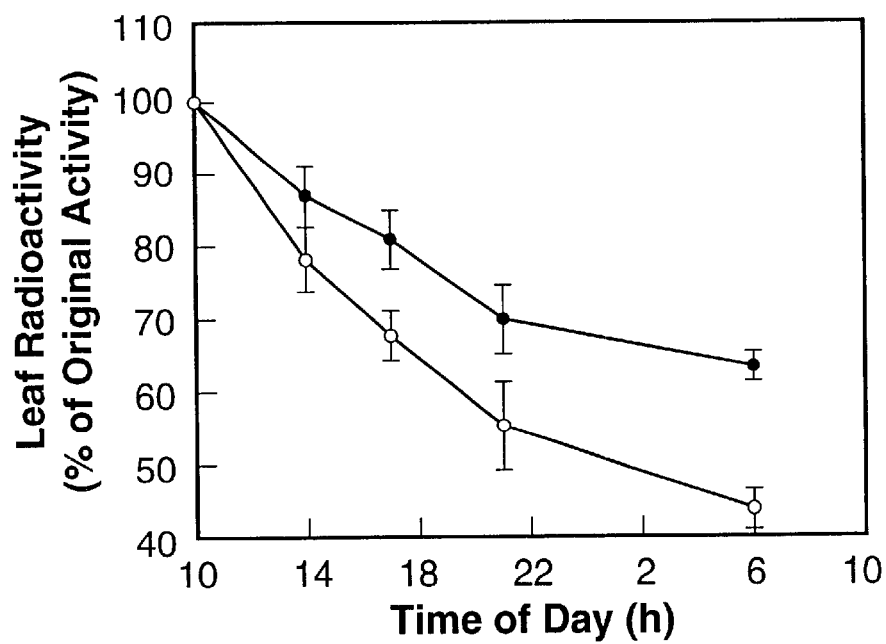
Figure 1C:
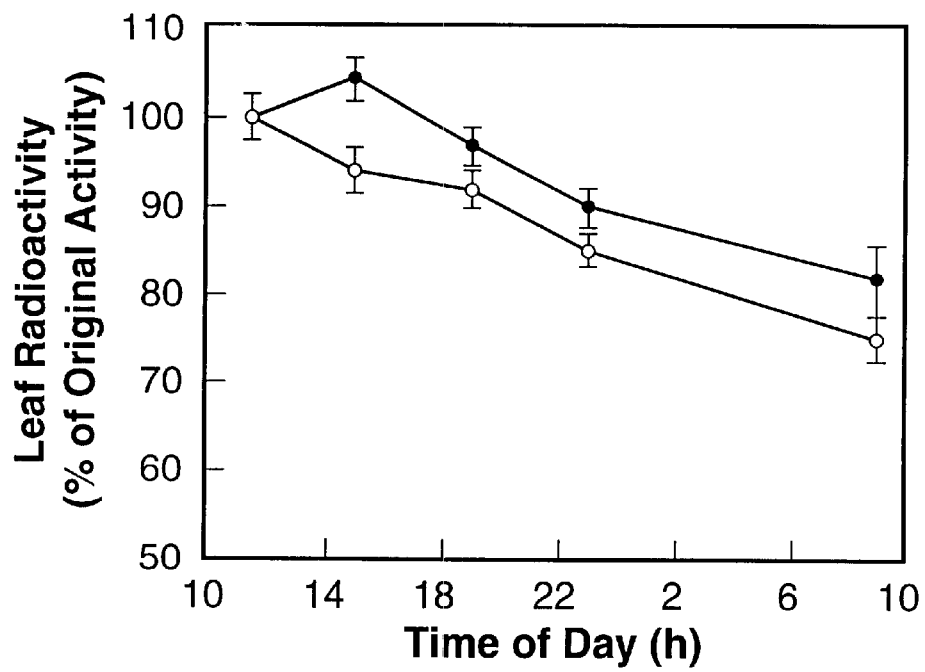

The invention may be better understood with reference to the accompanying drawings, in which:

FIGS. 1A, 1B and 1C illustrate diurnal changes in $^{14}$C-photosynthates in leaves of TMV-MP transgenic (●) and vector control (○) tobacco plants, experiments being performed on fully expanded source leaves (#5 and 6) (1A and 1B) or on younger, expanding source leaves (#2 and 3) (1C);

FIGS. 2A, 2B, 2C, 2D, 2E, 2F, 2G, 2H, 2I and 2J illustrate carbohydrate content and $^{14}$C-radioactivity detected within source leaves of transgenic tobacco plants expressing wild-type TMV-MP (line 277; ■), temperature-sensitive TMV-MP mutant (line 2–72; _) and vector control (line 306; ○), with radioactivity detected using a "Rotem" β counter (FIGS. 2A & 2B) and leaf discs analyzed for starch (FIGS. 2C & 2D), sucrose (FIGS. 2E & 2F), glucose (FIGS. 2G & 2H) and fructose (FIGS. 2I & 2J); and FIG. 3 is a schematic diagram illustrating sites where the TMV-MP might interact with the plant's endogenous control network to cause the observed alterations in sugar metabolism and reallocation of photosynthate to yield a reduction of root-to-shoot ratio in transgenic plants expressing the TMV-MP gene.

FIG. 4 is a schematic diagram in conventional single-letter amino acid code, showing the positions of mutations for different alanine scanning mutants of wild type KN1

DETAILED DESCRIPTION OF PREFERRED EMBODIMENTS

The results of research reported herein demonstrate that macromolecular trafficking of proteins and oligonucleotides via plasmodesmata is involved in control of enzyme function and gene expression. Modulation in this intercellular transport pathway can therefore be used to alter plant performance. Such alterations in macromolecular signalling can be used to redirect available resources, such as fixed carbon, nitrogen compounds (including amino acids) and mineral nutrients, as well as foreign compounds, to specific tissues within the plant. This invention provides compositions and methods which enable one skilled in the art to control this macromolecular trafficking and, thereby, control the rate and direction (e.g., to particular organs of the plant) of resource allocation.

For purposes of the present invention, a "plant regulatory composition" comprises at least one active agent which affects the growth and/or metabolism of the plant. The composition may comprise one or more polypeptides and/or oligonucleotides encoding such polypeptides as an active agent. In accordance with one preferred class of embodiments of the invention, the plant regulatory composition comprises at least one polypeptide and at least one oligonucleotide operatively encoding the polypeptide.

The active agent may comprise an endogenous or exogenous polypeptide or glycoprotein, including both heretofore known products and newly-engineered ones (e.g., mutant forms, fusion or chimeric proteins, etc.). Exemplary classes of products include, but are not limited to, the following: growth factors (e.g., KNOTTED-1 as discussed in detail herein); herbicides; insecticides; fungicides; agents against nematode infection; compounds which block herbivory; and compositions which enhance endogenous mechanisms involved in the establishment of general systemic acquired resistance in plants.

The range of applicability of the present invention may be better appreciated by consideration of representative types of agents suitable for incorporation into a plant regulatory composition. An example of a compound which blocks herbivory is the molecule systemin, which is a proteinase inhibitor [Ryan C. A. (1992) The search for the proteinase inhibitor-inducing factor, PIIF. *Plant Mol. Biol. Int. J. Mol. Biol. Biochem. Genet. Eng.* 19, 123–133; Constabel C. P., Bergey D. R., Ryan C. A. (1995) Systemin activates synthesis of wound-inducible tomato leaf polyphenol oxidase via the octadecanoid defense signaling pathway. *Proc. Natl. Acad. Sci. USA* 92, 407–411]. Systemin is a peptide of 18 amino acids [McGurl B., Pearce G., Orozco Cardenas M. L., Ryan C. A. (1992) Structure, expression, and antisense inhibition of the systemin precursor gene. *Science* 255, 1570–1573; Ryan C. A., McGurl B. (1992) The organization of the prosystemin gene. *Plant Mol. Biol. Int. J. Mol. Biol. Biochem. Genet. Eng.* 20, 405–409; Pearce G., Johnson S., Ryan C. A. (1993) Structure-activity of deleted and substituted systemin, an 18-amino acid polypeptide inducer of plant defensive genes. *J. Biol. Chem.* 268, 212–216] that is released when the plant is attacked by chewing insects (or as a result of physical injury). This small peptide moves into the phloem [Narvaez-Vasquez J., Pearce G., Orozco-Cardenas M. L., Franceschi V. R., Ryan, C. A. (1995) Autoradiographic and biochemical evidence for the systemic translocation of systemin in tomato plants. *Planta* 195, 593–600] and is thereby transported to regions where growth is taking place. Within these tissues, systemin acts on gene expression to turn on defense genes, including Proteinase Inhibitor I and II [Ryan 1992, supra]. Thus, a plant regulatory composition, in the case of this herbivory blocker, would comprise an oligonucleotide coding for: systemin; defense genes such as Proteinase Inhibitor I and II; and, a movement protein specific for movement of its coding oligonucleotide through plasmodesmata.

Modulations in plant growth or metabolism can be effected via regular utilization of transgenic plants which express an endogenous or exogenous gene, from a plant or other source. The creation and use of modified pathogenic genes and/or the development and expression of artificial genes that can mimic or override the functions performed by endogenous plant proteins encoded by the parent gene are also all clearly contemplated as within the scope of the present invention.

All processes that are controlled by this novel signal transduction pathway, involving plasmodesmal macromolecular transport, can be modified to alter plant function. Furthermore, novel molecules can be engineered to utilize this cell-to-cell and phloem long-distance transport route. Such a strategy will allow for the effective delivery of xenobiotic agents for control of a wide range of pests, as well as modified or genetically engineered plant proteins that will potentiate control over gene expression and cellular physiology.

In Example 1, the influence of the 30-kDa movement protein of tobacco mosaic virus (TMV-MP) on carbon partitioning in transgenic tobacco plants (*Nicotiana tabacum L.* cv Xanthi) expressing the TMV-MP was investigated. Using reciprocal grafting of transgenic tobacco plants expressing this movement protein and vector control plants, as well as transgenic tobacco plants expressing the TMV-MP in phloem cells only, it was shown that the interactive site involved in carbon allocation to roots is localized to the mesophyll tissue. Biomass partitioning experiments conducted on transgenic plants in which various deletion mutant forms of the TMV-MP (two of which included deletions in the domain responsible for increasing the size exclusion limit) were expressed revealed that the TMV-MP exerts its influence over carbon allocation via a mechanism that is completely independent of the TMV-MP-induced increase in plasmodesmal size exclusion limit. Furthermore, small N-and C-terminal deletions in the MP revealed the complexity in the interactions likely involved between the MP and an endogenous regulatory mechanism. The TMV-MP thus interferes with an endogenous signal transduction pathway that involves macromolecular trafficking through plasmodesmata to regulate biomass partitioning between the source and various sink tissues.

In Example 2, transgenic tobacco plants (*Nicotiana tabacum L.* cv. Xanthi) expressing wild-type or mutant forms of the 30-kDa movement protein of tobacco mosaic virus (TMV-MP) were employed to study the effects of the TMV-MP on carbon metabolism in source leaves. Fully expanded source leaves of transgenic plants expressing the TMV-MP were found to retain more newly fixed $^{14}C$ compared with control plants. Analysis of $^{14}C$-export from young leaves of TMV-MP plants, where the MP is yet to influence plasmodesmal size exclusion limit, indicated a similar pattern, in that daytime $^{14}C$ export was slower in TMV-MP plants as compared to equivalent-aged leaves on control plants. Pulse-chase experiments were used to monitor radioactivity present in the different carbohydrate fractions, at specified intervals following $^{14}CO_2$ labeling. These studies established that the TMV-MP can cause a significant adjustment in short-term $^{14}C$-photosynthate storage and export. That these effects of the TMV-MP on carbon metabolism and phloem function were not attributable to the effect of this protein on plasmodesmal size exclusion limits, per se, was established using transgenic tobacco plants expressing temperature-sensitive and C-terminal deletion mutant forms of the TMV-MP. Collectively, these studies establish the pleiotropic nature of the TMV-MP in transgenic tobacco. The results suggest potential sites of interaction between the TMV-MP and endogenous processes involved in regulating carbon metabolism and export.

As reported in Example 3, coinjection of KN1 and fluorescently labelled Knotted mRNA resulted in the efficient transport of mRNA from the target cell into the cells of the surrounding tissues. As expected, injection of fluorescently labelled Knotted mRNA alone resulted in the confinement of the fluorescent probe to the injected cell. Further, coinjection of the nonfunctional KN1 M11Y51 mutant and fluorescently labelled Knotted mRNA also resulted in the mRNA being confined to the target cell. This clearly demonstrates that a plant-encoded protein engages in its own cell-to-cell transport, as well as the transport of its mRNA.

In Example 4, it is shown that TMV-MP alters plant growth response to light intensity. When vector control, wild type and deletion mutant forms of TMV-MP transgenic plants were grown under high light conditions the wild type showed slight reductions in height and weight compared with the control. But, the deletion mutant exhibited an extremely different phenotype from the other two: plant height and total dry weight were greatly reduced. However, mean internodal length was not affected, and the root-to-shoot ratio of the deletion mutant was similar to that of the wild type. Then, under low light conditions, all three plant lines showed reduced root-to-shoot ratios, but the difference between transgenic and control plants seen under high-light conditions was not carried through; values for all three lines were the same. Yet, regarding internodal length and plant height, control plants increased in both; and, the wild type increased in the former, but not in the latter. The deletion mutant showed no response to low light.

In Example 5, an analysis of movement of the protein and RNA encoded by the maize knotted1 (kn1) homeobox gene (8) is reported. In situ and immunolocalization experiments show that the protein product, KN1 moves between adjacent cell layers. Microinjection studies in maize and tobacco show similar results. And comparison of wild type with various alanine scanning mutants of KN1 showed the mutants to have a reduced capacity to dilate plasmodesmata and potentiate their own cell-to-cell transport.

The present invention has immediate practical value in more precise characterization of the molecular steps involved in the process of macromolecular transport. This will then potentiate efficient manipulation of resource allocation without the complications associated with traditional genetic approaches.

The invention may be better understood with reference to the accompanying examples, which are intended for purposes of illustration only and should not be construed as in any sense limiting the scope of the present invention as defined in the claims appended hereto.

EXAMPLES

Example 1

Transgenic *Nicotiana tabacum L.* cv Xanthi expressing the TMV-MP and various deletion mutant forms of the MP were obtained from Dr. Roger Beachy, Scripps Institute, La Jolla, Calif.

Transgenic line 277 expressed the TMV-MP, while line 306 was a control which contained only the plasmid vector [Deom et al. 1987, supra]. Details relating to the different mutant forms of the TMV-MP utilized in this example are provided in Table 1. Transgenic lines 277 and 306 were used in the graft experiments. Most plant lines were $R_5$ to $R_8$ and were homozygous for the MP construct. In addition, it was already confirmed that the effects of the TMV-MP on carbon metabolism and biomass partitioning were not due to somaclonal variation or position effects associated with insertion sites [Lucas et al. 1993, supra]. The results obtained on the independent transformed tobacco plants used in the present study, which involved a wide range of TMV-MP mutants (see Table 1), further confirmed this finding.

Seeds were germinated on a soil mix, and after four weeks, seedlings were transplanted into 17.5 cm diameter plastic pots containing Yolo sandy loam. Plants were watered with ½x Hoagland's solution [Hoagland D. R. & Arnold D. I. (1938) The water-culture method for growing plants without soil. *California Agricultural Experimental Student Circular* 357, 1–39] twice daily. Five to six weeks after transplanting (70–75 days post germination), plants were separated into leaves, stems and roots and dried at 70° C. for 2 days. Dry weights were used to calculate tissue biomass and to compute root-to-shoot ratios. Routine measurements of photosynthetic rates were made during all growth experiments using a portable infra-red gas-exchange system (model LI-6200; LiCor, Lincoln, Nebr.). A fully developed leaf (leaf #5, leaf #1 being the youngest leaf to reach 5 cm at the time of measurement) was enclosed in a 1-1 chamber such that a 12-$cm^{-2}$ area was illuminated (Schott illuminator, KL-1500, Walz, Germany; approx. 1000 $\mu$mol $m^{-2}$ $s^{-1}$). The $CO_2$ concentration in the chamber varied between 350–370 ppm and relative humidity ranged between 30–45%. $CO_2$ uptake was measured and using the above parameters, rates of $CO_2$ exchange were computed.

Plants used in experiments reported in Tables 3 and 4 were grown in a greenhouse under autumn conditions (September–November; 10 hours natural sun light). Light intensities at mid-day ranged between 1200 and 1500 $\mu$mol $m^{-2}$ $s^{-1}$, whereas during the early morning and at dusk, the light intensity was about 400 $\mu$mol $m^{-2}$ $S^{-1}$. To extend the photoperiod, these plants were supplemented with light from high intensity metal halide lamps (600–700 $\mu$mol $m^{-2}$ $s^{-1}$) during the last 4 hours of a 14 hour day. Day/night temperatures were 26° C.±3.0/18° C.±4.0, respectively. These biomass partitioning experiments were repeated on plants grown under summer conditions (May–August; environmental conditions as for Tables 2 and 6). In graft, TMV-infection and C-terminal deletion (10 amino acids) (Tables 2, 6, and 7), plants were grown under the longer photoperiods of mid-summer (16 hours). Light intensity at mid-day was 1200–1500 $\mu$mol $m^{-2}$ $s^{-1}$, while in the morning and evening values ranged between 700–950 $\mu$mol $m^{-2}$ $s^{-1}$. Further, these plants were subjected to 30° C. ±5.0/22° C.±2.0 day/night temperature regimes, conditions that were directly comparable to those previously employed [Lucas et al. 1993, supra]. In all experiments, the location of a particular plant was selected at random in order to compensate for any minor variation in microclimate within the greenhouse.

Stocks and scions of MP-expressing transgenic tobacco line 277 and vector control line 306 were grafted, reciprocally. A "v" shaped notch was cut in the stem of the stock plant after removing the shoot at the second or third internode above the soil line. The lower remaining leaves on the stock were removed and the scion stem base was cut to a wedge and then inserted into the notch made in the stock. Both scion and stock were held together at the graft region using tygon tubing. The lower mature leaves on the scion were removed to reduce transpiration. The grafted plants were maintained in a mist chamber for two to three weeks until the graft had fused. Day/night temperatures in the mist chamber were 25° C./18° C., respectively. Grafted plants were then transferred to the greenhouse where they were grown for a further three weeks before being harvested for dry matter partitioning analysis.

For detection of TMV-MP in plants expressing the TMV-MP gene under phloem specific rolC promoter, leaf tissues of transgenic plant lines RMN-1, RMn-1, 277 and of vector control line 306 were extracted in lithium-phosphate buffer (50 mM) containing iodo-acetic acid (2.0 mM) and 2-mercaptoethanol (120 mM, pH 7.2) with a ratio of 1 g of tissue to 7 ml of buffer. Levels of TMV-MP in all other lines employed in the present study were well established in earlier reports [Deom et al. 1987, supra; Wolf et al. 1989, supra; Wolf S., Deom C. M., Beachy R. N. & Lucas W. J. (1991) Plasmodesmatal function is probed using transgenic tobacco plants that express a virus movement protein. *Plant Cell* 3, 593–604; Berna A., Gafny R., Wolf S., Lucas W. J., Holt C. A. & Beachy R. N. (1991) The TMV movement protein: Role of the C-terminal 73 amino acids in subcellular localization and function. *Virology* 182, 682–689; Gafny R., Lapidot M., Berna A., Holt C. A., Deom C. M. & Beachy R. N. (1992) Effects of terminal deletion mutations on function of the movement protein of tobacco mosaic virus. *Virology* 187, 499–507; Lapidot M., Gafny R., Ding B., Wolf S., Lucas W. J. & Beachy R. N. (1993) A dysfunctional movement protein of tobacco mosaic virus that partially modifies the plasmodesmata and limits virus spread in transgenic plants. *The Plant Journal* 4, 959–970]. The leaf homogenate was centrifuged at 10,000 g for 10 minutes, and soluble (cytoplasm) as well as insoluble (cell wall and membranes) fractions were separated. Proteins in both of these fractions were separated by one-dimensional polyacrylamide gel-electrophoresis. Electrophoretic blotting procedures were followed as described [Towbin H., Staehelin T. & Gordon J. (1979) Electrophoretic transfer of proteins from polyacrlamide gels to nitrocellulose sheets: Procedure and some applications. *Proc. Natl. Acad. Sci. USA* 76, 4350–4354] with some modifications. Proteins were transferred onto Immobilon membrane (Millipore), which was then blocked in bovine serum albumin for one hour. The membrane was then incubated in phosphate-saline buffer containing antibody raised against the TMV-MP. The cross-reaction between the 30-kDa TMV-MP and the antibody against the TMV-MP was observed by color reaction using horse radish peroxidase as the secondary antibody.

Tobacco plants (lines 306 and 277) having six fully expanded leaves (mid-summer-grown plants) were inoculated on the 4th leaf (counting from the top) with 0.5 mg ml$^{-1}$ TMV in phosphate buffer (pH 7.2) using Carborundum (400 mesh). Plants were transferred to shade conditions (light intensity approx. 150 $\mu$mol m$^{-2}$ s$^{-1}$) for two days before being returned to normal full sunlight conditions in the greenhouse (see above for growth conditions). Symptom development was recorded and at the time of harvesting the plants had 12–14 systemically infected leaves, showing normal chlorotic-mosaic symptoms associated with TMV infection.

To ascertain whether the TMV-MP is required, in both shoots and roots, to exert its influence over biomass partitioning, a series of graft experiments were conducted. Shoots of transgenic line 277, in which the TMV-MP was being expressed, were grafted on vector control line 306, and vice versa. As illustrated in Table 2, when the scion (shoot) was 277 in nature, the root-to-shoot ratio was low, whereas when the scion was from line 306, the root-to-shoot ratio was relatively high and comparable to values obtained on grafted plants in which both scion and stock were derived from line 306 (Table 2). These results established that the TMV-MP was only required in source leaf tissues in order for it to alter the root-to-shoot ratio.

To further refine the site(s) of interaction between the TMV-MP and the putative endogenous control system that regulates carbon partitioning, transgenic plants were employed in which expression of the TMV-MP was confined to cells of the phloem (vasculature). The presence of the TMV-MP in these plant lines (RMn-1 and RMN-1) was confirmed by western blot analysis using antisera against the TMV-MP. As illustrated in the data presented in Table 3, when the TMV-MP was localized to the phloem, such plants were similar in phenotype to the vector control line (cf. lines RMn-1, 306 and 277). Note that although the leaf biomass was similar in lines 306, 277 and RMn-1, stem and root mass was significantly lower in line 277 compared with lines 306 and RMn-1. A second experiment was performed, in which Xanthi NN plants were used, and again, as shown by the data presented in Table 3, expression of the TMV-MP within the phloem tissues had no detectable influence over plant weight, leaf, stem and root mass, or carbon partitioning, as reflected by the root-to-shoot ratio. These data suggest that the TMV-MP had only to be present in the mesophyll tissue in order to exert its influence over carbon allocation.

Earlier studies established that the influence of the TMV-MP, in terms of increasing the SEL of secondary plasmodesmata, was also restricted to the mesophyll and mesophyll/bundle-sheath boundaries [Ding et al. 1992, supra]. To explore whether a direct relationship existed between the ability of the TMV-MP to increase plasmodesmal SEL and to alter biomass partitioning, experiments were performed on a range of MP deletion mutants that spanned the domain in the TMV-MP (amino acids 195–213) responsible for the dilation of secondary plasmodesmata [Berna et al. 1991, supra]. Since these mutant forms of the TMV-MP were expressed in tobacco genotypes nn and NN (isogenic, or near isogenic lines), non-transformed tobacco plants were first analyzed, and it was found that biomass partitioning and root-to-shoot ratios were comparable in both genotypes. It was next established that both genetic lines yielded statistically identical biomass partitioning results in terms of non-transformed and vector control transformed plants.

The first two TMV-MP deletion mutants used in this series of experiments (lines MN-1 and MN-2) had the C-terminal 33 and 55 amino acids deleted, respectively, but they still retained the ability to dilate plasmodesmata to the level detected in TMV-MP transgenic plants [Berna et al. 1991, supra]. As shown in Table 4, transgenic tobacco line MN-1 showed a slight reduction in its ability to override the endogenous control over carbon partitioning, when compared with that of the full-length TMV-MP. In transgenic tobacco line MN-2, a minor alteration in the ability of the mutant TMV-MP to reduce carbon allocation to the lower stem and roots was also observed. A deletion within the SEL domain of the TMV-MP (line Mn-3) had no significant effect on growth or root-to-shoot ratios, when compared with values obtained on line 277. Furthermore, a similar result was obtained when the entire SEL domain was removed (line Mn-4; see Table 4). Note that in mutant lines Mn-3 and Mn-4 the plasmodesmal SEL was identical to line 306, being approx. 900 Da.

To further explore the relationship between SEL and alteration in carbon allocation, biomass partitioning experiments were performed on a mutant form of the TMV-MP in which amino acids 3–5 had been deleted from the N-terminus [Lapidot et al. 1993, supra]. Transgenic tobacco plants expressing this mutant (line Mn-5) exhibited a reduced SEL of 3.9 kDa compared with 9.4 kDa in plant line 277 [Lapidot et al. 1993, supra]. Interestingly, these plants showed an even more drastic phenotype, with leaf, stem and root mass being reduced to 50% of the values measured in plant line 277. This reduction in plant biomass was not due to an effect of the mutant TMV-MP on photosynthesis, as under the growth conditions used in the present study, transgenic plants expressing all forms of the TMV-MP had measured photosynthetic rates that were comparable to the rates measured in control lines; i.e., 11.6 $\mu$mol $CO_2$ $m^{-2}$ $s^{-1}$. It is interesting to note that even though Mn-5 had an overall reduction in biomass partitioning, root-to-shoot ratios were comparable to those measured in 277 and other lines expressing mutant forms of the TMV-MP. Transgenic line Mn-6 represented an ideal internal control for the latter experiment, as this line did not contain detectable levels of TMV-MP, although the gene was present in these plants [Lapidot et al. 1993, supra]. These plants showed similar characteristics of biomass partitioning and root-to-shoot ratios when compared with vector control line 306 (see Table 4).

As part of the growth analysis, performed on the transgenic tobacco plants expressing the various mutant forms of the TMV-MP, plant height and number of leaves were measured at the time of harvest. The data presented in Table 5 are consistent with the conclusions drawn from biomass data presented in Table 4. Interestingly, mutant line MN-2 again showed signs of reverting towards the phenotype of vector control plants. However, in all other respects these data indicated that the influence of the TMV-MP on plant growth (as reflected by plant height and leaf number) was independent of the TMV-MP-induced change in plasmodesmal SEL. Note again that whereas Mn-5 represented the smallest phenotype, with the fewest leaves, plant line Mn-6 was identical to the vector control line 306. Collectively, these results established that the TMV-MP-induced alteration in carbon allocation was not associated with the ability of the TMV-MP to increase plasmodesmal SEL.

Over the course of these experiments, plants were grown under both summer (May–August) and autumn (September–November) conditions. While each repeat experiment confirmed the explicit influence of the TMV-MP on biomass partitioning and root-to-shoot ratio, the absolute values displayed a trend in which all values were larger in summer grown plants.

In view of the established significant effects that the TMV-MP has when constitutively expressed in transgenic tobacco plants, the effect of the TMV-MP produced during normal plant infection by TMV was explored. As illustrated in Table 6, TMV infected 306 plants had reduced root biomass and their subsequent root-to-shoot ratio was also lowered from the uninfected control value of 0.11 to 0.07 (i.e., a value identical to that measured on the uninfected 277 plant line). Interestingly, TMV infection of plant line 277 failed to further reduce root mass or root-to-shoot ratio. These results establish that the TMV-MP produced in the course of infection results in an identical effect on biomass partitioning as that observed when the TMV-MP is constitutively expressed in transgenic plants. Since TMV infection of 277 plants failed to further influence biomass partitioning, in the presence of TMV-MP expressed within these plants, it would appear that the level of the MP in plant line 277 is already at a sufficient level to exert its full influence over the TMV-MP induced alteration in carbon allocation to the roots.

The effect of a small, C-terminal 10 amino acid, deletion in the TMV-MP on sugar metabolism was investigated. Transgenic plants expressing this mutant form of the MP exhibited a normal pattern of sugar metabolism with sucrose, glucose, fructose, and starch levels all reflecting diurnal patterns equivalent to control plant line 306. In view of this important finding a parallel study was performed to determine the effect of this mutant TMV-MP on biomass partitioning. As illustrated in Table 7, two independently transformed lines (Mn-1 and Mn-2) exhibited statistically identical biomass partitioning characteristics. Note that in this experimental series, plant line 277 had a root-to-shoot ratio of 0.07 whereas both plant lines Mn-1 and Mn-2 had root-to-shoot ratios of 0.10 to 0.12, which were statistically identical to the value of 0.11 measured on plant line 306. Western blot analysis indicated that the level of TMV-MP in Mn-1 and Mn-2 was approximately 25% of that in line 277. This level is consistent with previous reports [Berna et al. 1991, supra]. These data establish that a C-terminal 10 amino acid deletion in the MP abolished its ability to alter both biomass partitioning and carbon export/sugar metabolism (Table 7). A comparison of growth characteristics between plant lines 306, Mn-1, Mn-2 and 277 also supported this conclusion in that the first three had identical characteristics, while 277 plants showed the same differences as previously illustrated in Table 5.

Based on the grafting experiments (see Table 2) and studies performed on transgenic plants in which expression of the TMV-MP was confined to the phloem (see Table 3), the presence of the TMV-MP within the mesophyll tissue is sufficient for it to exert its influence over carbon allocation and biomass partitioning within the plant. The observation that normal root-to-shoot ratios (equivalent to vector control RGN-1, 3001 and 306) were present in plants in which the TMV-MP was restricted to the phloem is consistent with previous findings establishing that the TMV-MP is ineffective within the phloem, in that it is unable to increase plasmodesmal SEL between the cells of the phloem [Ding et al. 1992, supra]. These results support the hypothesis that the TMV-MP is required, specifically, in mesophyll tissue in order to exert its effects over biomass partitioning.

Recent studies provided direct experimental proof that viral MPs have the capacity to effect their trafficking through mesophyll plasmodesmata [Fujiwara T., Giesman-Cookmeyer D., Ding B., Lommel S. A. & Lucas W. J. (1993) Cell-to-cell trafficking of macromolecules through plasmodesmata, potentiated by the red clover necrotic mosaic virus movement protein. Plant *Cell* 5, 1783–1794; Noueiry A. O., Lucas W. J. & Gilbertson R. L. (1994) Two proteins of a plant DNA virus coordinate nuclear and plasmodesmal transport. *Cell* 76, 925–932; Waigmann et al. 1994, supra]. In view of this property, the possibility exists that movement proteins synthesized within the leaf may undergo extensive trafficking into all of the surrounding tissues. Clearly, if the TMV-MP could traffic from vascular into mesophyll tissue, a change should have been observed in root-to-shoot ratio in plant line RMn-1 and RMN-1. The absence of such an effect is consistent with the observation that macromolecular trafficking through plasmodesmata is always correlated with an increase in SEL to 9.4 kDa or above. The inability of the TMV-MP to interact with phloem plasmodesmata to cause such an increase in SEL [Ding et al. 1992, supra] implies that the protein would not be able to traffic within this tissue, nor would it be capable of exiting across the bundle-sheath plasmodesmata to enter the mesophyll. The trafficking of TMV-MP, located in the mesophyll, would similarly be restricted to plasmodesmal transport within this tissue, but also would include transport into the bundle-sheath cells [Ding et al. 1992, supra]. Thus, the mechanism by which the TMV-MP elicits a change in biomass partitioning most likely involves a perturbation to an endogenous control mechanism that originates from within the mesophyll.

The experiments performed on transgenic plants expressing mutant forms of the TMV-MP show that the TMV-MP-induced alteration in carbon partitioning is independent of the effect of the ability of this MP to interact with and increase the SEL of mesophyll secondary plasmodesmata. C-terminal deletion mutations both inside and at the borders of the MP domain associated with increasing the plasmodesmal SEL [Lucas W. J. & Gilbertson R. L. (1994) Plasmodesmata in relation to viral movement within leaf tissues. *Annual Review of Phytopathology* 32, 387–411] had little or no effect on carbon partitioning, as reflected by biomass partitioning and root-to-shoot ratios (see Table 4). Indeed, removal of both the C-terminal 73 and 116 amino acids from the TMV-MP (line Mn-3 and Mn-4) prevented these mutant MPs from entering the plasmodesmata, with most of the protein residing in the soluble (cytoplasmic) fraction [Berna et al. 1991, supra]. Yet, transgenic plants expressing these mutant forms of the TMV-MP had root-to-shoot ratios equivalent to plant line 277.

The most pronounced effect on the phenotype of transgenic tobacco plants expressing the TMV-MP was observed in plants expressing a mutant form in which the N-terminal 3–5 amino acids were deleted. These plants exhibited an overall reduction in plant morphology in comparison to control line 306 (see Table 5). This effect is quite remarkable given that the level of MP in the mesophyll tissue of plant line Mn-5 was approximately $\frac{1}{20}$th of that measured in plant line 277. Additionally, Mn-5 was dysfunctional, in that although it entered the plasmodesmata, the levels were extremely low (below the detectable limits of immunocytochemistry) [Lapidot et al. 1993, supra], and it was incapable of increasing the SEL beyond 3.9 kDa. Again, the influence of this movement protein on biomass partitioning is inconsistent with a simple increase in plasmodesmatal SEL.

The influence of Mn-5, on the overall phenotype of the plant, suggests that the N-terminus of the TMV-MP may contain a domain which interacts with an endogenous regulatory mechanism involved in carbon partitioning. This would imply that the C-terminal portion of the MP serves to mediate in viral systemic infection. This conclusion is supported by the recent finding that the N-terminal 1–126 amino acids are completely dispensable in terms of TMV-MP trafficking through mesophyll plasmodesmata [Waigmann et al. 1994, supra]. Furthermore, transgenic plants expressing the MP of cucumber mosaic virus (CMV-MP), which has a C-terminus that is similar to that of TMV-MP, had no effect on plant phenotype or root-to-shoot ratio.

As the level of the TMV-MP in plant lines Mn-1 and Mn-2 was lower (approx. 25%) than that detected in line 277, the possibility must be considered that this level is insufficient to effect any change in biomass partitioning. Since the TMV-MP in lines Mn-1 and Mn-2 caused "normal" TMV-MP-induced increase in plasmodesmal SEL and complemented infection by a TMV (-MP) construct [Berna et al. 1991, supra], it would appear that adequate MP is present within the mesophyll tissue. This conclusion is also supported by the fact that plant line Mn-3, which had a comparable level of TMV-MP to plant lines Mn-1 and Mn-2 [Berna et al. 1991, supra], exhibited root-to-shoot ratios equivalent to those observed in plant line 277 (see Table 4). In addition, plant line Mn-5, which had MP levels of approx. $\frac{1}{20}$ of those present in plant line 277, exhibited biomass partitioning equivalent to plant line 277 (Table 4). Finally, parallel sugar and starch analysis, performed on these deletion mutant plant lines, revealed equivalent levels within plant lines Mn-3, Mn-4 and 277.

The important point established by studies on plant lines Mn-1 and Mn-2 is that a common site of action, in the endogenous regulatory mechanism, may be involved in mediating the TMV-MP-induced alteration in both sugar metabolism and biomass partitioning. Alternatively, the influence of the TMV-MP could reflect a direct effect on one physiological process with a secondary effect on the other. The complexity of these regulatory signals involved in the orchestration of carbon metabolism and partitioning was also illustrated by the finding that sink strength could override the effect of the TMV-MP on net carbon export, but did not negate the influence of the MP on sugar accumulation in mature source leaf.

The present results establish that the TMV-MP exerts its effect on carbon allocation and biomass partitioning from a site located within the mesophyll tissue. Further, the mode of action of the TMV-MP, in terms of altering biomass partitioning and root-to-shoot ratio, appears to be completely independent of the mechanism by which this MP acts to increase the SEL of mesophyll secondary plasmodesmata. Finally, source leaves of TMV-MP transgenic tobacco plants have elevated levels of sugars and starch, although their photosynthetic rates are equivalent to control lines, suggesting that either the transport of sugars out of the leaf is reduced, or that photosynthate metabolism (sugars and starch) is affected.

Several possible mechanisms can be postulated to account for the way in which the TMV-MP alters carbon allocation and biomass partitioning. One possible site for these effects might be located at the plasmodesmata where the MP may interfere with sucrose movement from the mesophyll into the phloem. However, there are presently no data consistent with active, vectorial, transport of sucrose (or any other small metabolite) through plasmodesmata. Nor is information available on whether sucrose interacts, directly, with any plasmodesmal protein(s).

The TMV-MP may exert its effects directly, or indirectly, by altering metabolism and/or membrane transport of sugars (glucose, fructose, sucrose, etc). Likely sites may reside at the chloroplast envelope, the tonoplast (mesophyll) or the plasma membrane (mesophyll and/or phloem), and involve an interaction between the TMV-MP and either the sugar transporter or regulatory elements that may control carbon allocation. Such an interaction may possibly explain the observed changes in glucose and fructose compartmentation, as well as starch metabolism, in TMV-MP transgenic tobacco plants. However, it is difficult to reconcile the MP-induced changes in sucrose levels on the basis of this model, as the major site of influence of the TMV-MP would have to be at the companion cell-sieve element complex where sucrose loading is thought to take place. This site of action is inconsistent with the experimental data reported herein, in that plants in which TMV-MP synthesis is restricted to the vascular tissue exhibit carbon allocation and biomass partitioning patterns that are identical to control plants (Table 3). This suggests that a more complex interaction may be involved in the regulation of photosynthate movement from the mesophyll to the companion cell-sieve element complex. Furthermore, the finding that the presence of the TMV-MP in leaf tissues (within the mesophyll) results in a significant reduction in biomass being partitioned to the lower stem and root tissues (Tables 2, 4 & 7) also implies the involvement of a complex regulatory mechanism for the control of photosynthate utilization.

In light of findings that plasmodesmata are capable of transporting endogenous proteins [Fisher D. B., Wu Y. & Ku M. S. B. (1992) Turnover of soluble proteins in the wheat sieve tube. *Plant Physiology* 100, 1433–1441] as well as viral proteins [Lucas & Gilbertson 1994, supra], a model based on this established macromolecular (protein, RNA/DNA) trafficking capability of higher plant plasmodesmata is proposed, wherein the companion cell-sieve element complex within the source leaf would function as the control center in terms of establishing priorities with respect to carbon delivery to various sinks throughout the plant. Further, photosynthesis and short-term carbohydrate storage, within the mesophyll, would be regulated by output signals (macromolecular) that traffic via plasmodesmata from the companion cell to the mesophyll, where they function by interacting with either sugar transport systems (tonoplast or chloroplast envelope) or key enzymes in the metabolic pathway leading to sucrose synthesis [Lucas W. J. & Wolf S. (1993) Plasmodesmata: the intercellular organelles of green plants. *Trends in Cell Biology* 3, 308–315]. The return loop of this signal transduction cycle would involve input signals from the mesophyll that are transported via plasmodesmata to the companion cell-sieve element complex. These input signals would act to "inform" the companion cell-sieve element complex of the status of photosynthesis within the mesophyll (i.e., current rate of net carbon fixation under prevailing conditions).

In the framework of this macromolecular trafficking signaling model, the TMV-MP would act as a competitive analogue to an endogenous protein that functions as an essential component of the input signal(s) that traffics, via plasmodesmata, from the mesophyll to the companion cell-sieve element complex. These two protein homologue (the TMV-MP and the endogenous input signaling protein) would compete for a common plasmodesmal binding site, with the TMV-MP reducing the transport of the endogenous input signal. A reduction in the level of this input signal (protein) is proposed to result in a change in protein synthesis (gene expression) within the companion cell, resulting in an alteration in both the rate at which sucrose is loaded into the phloem and the set-point [Mooney & Winner 1991, supra] in carbon delivery to the roots. The change in set-point for carbon delivery would involve a modulation in trafficking of proteins from the companion cell to the sieve element. The immediate result of the change in phloem loading would be an increase in sucrose levels (on a diurnal basis) within the mesophyll [Lucas et al. 1993, supra]. The alteration in the set-point of biomass partitioning, mediated by a change in the delivery of informational macromolecules to the root (via the phloem), would give rise to plants having a significant reduction in root-to-shoot ratios (Tables 3, 4 & 6).

The experimental results presented in Tables 4 and 5 provide support for the claim that control can be exerted over plant development through an interaction with plasmodesmal macromolecular trafficking. In this case, transgenic plants expressing mutant forms of the TMV-MP exhibited an overall reduction in plant growth. This was the direct result of expressing a mutant form of the TMV-MP in which amino acids 3,4 & 5 had been deleted (mutant Mn-5 in Tables 4 & 5). In these transgenic tobacco plants, the presence of a dysfunctional Mn-5 TMV-MP gave rise to a down-regulation of overall plant growth. Whereas leaf number was little affected, total plant weight and plant height were reduced to 41% and 55%, respectively, of control plants (Tables 4 & 5). A comparison between these results and those obtained with plants expressing a C-terminal 10 amino acid deletion mutant of the TMV-MP (see Table 7), establish that the effects on plant growth must be directly attributable to the presence of the mutant form of the TMV-MP.

These results establish that expression of a dysfunctional form of a protein that has the molecular properties to enable it to interact with and/or traffic cell-to-cell through plasmodesmata can be used to control overall plant size. Manipulation of such dwarf characteristics should have general application in horticultural practices.

Example 2

Transgenic tobacco plants (*Nicotiana tabacum* L. cv. Xanthi) expressing wild-type (plant lines 277 [Deom et al. 1987, supra] and 2004 [Deom et al. 1991, supra], temperature-sensitive mutant (ts, MPP 154A) line 2–72 [Wolf et al. 1991, supra] and C-terminal (10 amino acids) deletion mutant line MP1 [Berna et al. 1991, supra] forms of TMV-MP, as well as vector control tobacco plants (lines 306, 3001; transformed but without the MP gene), were used in the present experiments. Three-week-old seedlings were transferred into plastic pots (15 cm diameter) and plants were grown in an insect-free, temperature-controlled greenhouse (approx. 25° C. day/ 18° C. night). In some experiments, the temperature within this same greenhouse was raised to 34° C./32° C. (day/night, respectively). Plants were grown under natural sunlight having a midday average photon flux density of 1500 $\mu mol.m^{-2} s^{-1}$.

Net photosynthesis (measured as $CO_2$ uptake) was determined using a closed-portable infrared gas exchanged system (LI-6200, LICOR Inc., Lincoln, Nebr., USA). An attached leaf was placed in a 1 l lexan chamber such that a 10 cm area was exposed to light and gas flow. The youngest fully expanded leaf (#5 or #6, with leaf #1 being the last leaf to achieve a length of 5.0 cm) was used in these experiments. All measurements (photosynthesis and respiration) were carried out on well-watered plants during the late morning h (10–12 noon) on bright, sunny days. The initial $CO_2$ concentration in the chamber was 340±10 $\mu l$ 1$^{-1}$, and a 30 s measurement was started immediately after a reduction in $CO_2$ concentration was detected. Dark respiration was measured by covering the leaf chamber with a black cloth and measurements were started immediately after an increase in $CO_2$ concentration was observed. Negative values of photosynthesis were interpreted as dark respiration.

Carbohydrate content within leaves was determined as previously described [Lucas et al. 1993, supra]. In brief, soluble sugars were extracted in 80% ethanol from leaf discs (1.5 cm$^2$). After evaporating the supernatant to dryness, sugars were redissolved in H$_2$O and then filtered through a 0.45 µm membrane (Whatman, Clifton, N.J., USA). Sugar separation was carried out on an analytical HPLC system (LDC Anal., Reviera Beach, Fla., USA), fitted with a Sugar-Pak I column (6.5 mm 300 mm; Waters Associates, Milford, Mass., USA) using an LDC refractive-index detector (Refractor Monitor IV). Starch content was determined on the ethanol-water extracted leaf discs following starch conversion by amyloglucosidase (Cat. No. A-7255; Sigma Chemical Co., St. Louis, Mo., USA). Starch content, as glucose equivalents, was measured using the Sigma (HK) quantitative glucose determination kit.

Tobacco leaves were labeled with $^{14}CO_2$ by using a pulse-labeling system. Experiments were carried out in the greenhouse, during the late morning h on bright days, under optimal photosynthetic conditions. An attached tobacco leaf was sealed into a 41 Plexiglas chamber where it was held between two layers of nylon monofilament. A volume of 60 cm$^3$ of $^{14}CO_2$ was then released into the chamber (40 s) to give an initial specific activity of $2 \cdot 10^5$ Bq·mg$^{-1}$ carbon. It took less than 20 min for the $CO^2$ concentration in this chamber to be reduced to the compensation point, by which time the $^{14}CO_2$ would have been assimilated into photosynthetic products. At this point, the leaf was released from the chamber and was used for analysis of $^{14}C$-photosynthate export.

Rate of reduction in radioactivity of either total leaf $^{14}C$ or $^{14}C$-labeled carbohydrates was determined from time course measurements that commenced immediately after a leaf was released from the $^{14}CO^2$-labeling chamber. Total radioactive content within each $^{14}C$-labeled leaf was determined using one of the following two methods. First, at various time intervals, leaf discs were punched from an attached leaf and were then dissolved in tissue solubilizer (Soluen-350; Packard Instrument Co., Inc., Downers Grove, Ill., USA). After 3–5 d the radioactivity was measured on a Betamatic liquid scintillation counter (Kontron Instrument, Zurich, Switzerland) using Ultima-gold scintillation cocktail (Packard Instrument Co.). Second, a portable, Geiger-Müller tube (RAM-DA, Rotem Industries, Be'er Sheva, Israel) containing a circled β counter, (Model GM-10, diam. 4 cm) was placed on the adaxial surface, to the side of the main vein, in the mid-region of an intact $^{14}C$-labeled leaf; data were collected (100 s sampling period) at appropriate times over a 24 h experimental period. A comparison between in planta β-radiation detection (Geiger-Müller) and scintillation-based $^{14}C$ analysis demonstrated that the two methods yielded data that were highly correlated over the range of radioactivity levels employed in the present experiments. Radioactivity within an intact leaf was assayed using the portable β counter system following $^{14}CO_2$ feeding. Then, three leaf discs were punched from the detection site and dissolved for 3–5 days in Soluene-350. Radioactivity within these discs was then assayed by scintillation spectrometry. In view of this finding, the portable β-radiation detector was used to perform non-destructive time course experiments on $^{14}CO_2$ pulse-labeled source leaves of TMV-MP transgenic (lines 277, 2004 and 2–72) and control (lines 306 and 3001) tobacco plants.

Partitioning of newly fixed carbon within leaf carbohydrates was determined in a manner that gave data on both concentration and radioactivity of each component. Sugars (sucrose, glucose and fructose) were identified and fractionated by HPLC. Radioactivity that eluted at the sample-front peak was collected separately and termed the liquid residue. Radioactivity in the starch fraction was measured after enzymatic conversion to glucose residues. Following carbohydrate extraction, the remaining leaf tissue was solubilized (Soluen-350) for 3–5 d prior to assaying for radioactivity (this fraction was termed the solid residue).

It has been established that TMV-MP transgenic plants (line 277) accumulated much higher amounts of carbohydrate during the day as compared to control tobacco plants (line 306); however, over the dark period, the level of all carbohydrates appeared to decline more rapidly in 277 than in 306 plants, often resulting in the establishment of comparable levels in both lines by the next morning [Lucas et al. 1993, supra]. The time course data presented in FIG. 1A indicate that the rate of reduction in radioactivity was significantly lower in TMV-MP-expressing tobacco leaves as compared to control plants. Plants were grown in a greenhouse (25°/18° C. day/night) under natural sunlight with a midday average photon flux density of 1500 µmol.m$^{-2}$.s$^{-1}$. Radioactivity within intact leaves was assayed non-destructively with a "Rotem" portable β counter. Experiments were performed on fully expanded source leaves (#5 and 6) (A, B) and on younger, expanding source leaves (#2 and 3) (C). Plant lines 277 and 306 were used for experiments in A and C, while plant lines 2004 and 3001 were employed in the experiments presented in B. Values represent mean±SE (n=5).

To further confirm the effect of the TMV-MP on the rate of reduction of $^{14}C$-labeled photosynthate, a similar series of experiments on transgenic tobacco plants that expressed the TMV-MP in a slightly different genetic background (N. tabacum Xanthi NN) was performed. Plants homozygous for the TMV-MP gene and which had levels of TMV-MP within leaf tissues that were comparable to those measured in TMV infected plants (plant line 2004) [Deom et al 1991, supra], were chosen for these studies. As illustrated in FIG. 1B, plant line 2004 also exhibited a slower rate of reduction in the level of radioactivity that remained in the source leaves compared with equivalent leaves on the respective vector control plants (line 3001).

Pulse-labeling experiments, performed on young leaves (leaf #2) in which the TMV-MP would not yet have caused an increase in plasmodesmal SEL [Deom, C. M., Schubert, K. R., Wolf, S., Holt, C. A., Lucas, W. J., Beachy, R. N. (1990) Molecular characterization and biological function of the movement protein of tobacco mosaic virus in transgenic plants. Proc. Natl. Acad. Sci. USA 87, 3284–3288; Ding et al. 1992, supra], demonstrated lower rates of reduction in the level of residual leaf radioactivity compared to fully expanded leaves (FIG. 1C). Although the rate of reduction of $^{14}C$ was similar between the two plant lines, line 277 consistently retained more $^{14}C$ photosynthate over a diurnal cycle (statistically significant at P=0.05). These findings are in full agreement with an earlier study performed on a completely independent TMV-MP transformant (line 274) [Lucas et al. 1993, supra].

Analysis of $^{14}C$-labeled and total photoassimilates revealed a significant difference between 277 and 306 plant lines (Table 8). During the daylight hours the sucrose levels in TMV-MP transgenic plants were almost double those of control plants (Table 8). In control plants, $^{14}C$-sucrose declined during the daylight hours to approximately 22% of the value measured shortly after the $^{14}CO_2$ labeling treatment; for plant line 277, this value decreased to only 50% over the same period. The decrease in $^{14}C$-sucrose in line 277 represented the major portion of the total loss of radioactivity, whereas in control plants it represented about half of the total loss. The other fraction contributing to the total decline of radioactivity in control leaves (306) was the liquid residue (Table 8).

Interestingly, $^{14}$C-glucose decreased by only 4% in line 277 compared with 30% in control plants, while in both lines $^{14}$C-fructose increased during the period after $^{14}$CO$_2$ labeling, with a subsequent decrease being detected only in control plants. As expected, $^{14}$C activity in the starch fraction remained relatively constant, in both lines, over the ensuing photoperiod. The solid residue fraction consisted of non-extractable metabolites and structural carbohydrates. Radioactivity in this component increased in both lines, probably due to turnover of cell wall components.

A temperature-sensitive (ts) TMV-MP, mutant MPP 154A, was generated by changing the proline residue at amino acid 154 of the TMV-MP to alanine [Wolf et al. 1991, supra; Leonard, D. A., Zaitlin, M. (1982) A temperature-sensitive strain of tobacco mosaic virus defective in cell-to-cell movement generates an altered viral-coded protein. *Virology* 117, 416–424; Ohno, T., Takamatsu, N., Meshi, T., Okada, Y., Nishiguchi, M., Kiko, Y. (1983) Single amino acid substitution in 30K protein of TMV defective in virus transport function. *Virology* 131, 255–258; Deom et al. 1987, supra; Meshi, T., Watanabe, Y., Saito, T., Sugimoto, A., Maeda, T., Okada, Y. (1987) Function of the 30 kDa protein of tobacco mosaic virus: Involvement in cell-to-cell movement and dispensability for replication. *EMBO J.* 6, 2557–2563]. Studies on plasmodesmal SEL in transgenic tobacco plants expressing this ts mutant TMV-MP (line 2–72) indicated that, under permissive temperatures (24° C.; i.e. temperatures that permitted infection of these plants by a MP- strain of TMV), the SEL was elevated to levels identical to those measured in wild-type TMV-MP transgenic plants (line 277). However, under non-permissive temperatures (32° C.), the SEL in plant line 2–72 was similar to that detected in control plants (line 306) [Wolf et al. 1991, supra]. Furthermore, this plant line was selected for the present study as homozygous plants were shown to express the ts-form of the TMV-MP to yield levels that were equivalent to those present in wild-type TMV-MP plants (lines 277, 274, etc.). Finally, previous studies on plant line 2–72 established that the ts TMV-MP did not undergo accelerated degradation under elevated temperatures [Wolf et al. 1991, supra].

Before examining the effects of temperature-induced alteration in TMV-MP-mediated increase in plasmodesmal SEL, it was necessary to ensure that temperature, per se, did not cause differential effects on photosynthesis or respiration in plant lines 277, 2–72 and 306. Photosynthesis and dark respiration measurements, performed on plants grown at 25° C. daytime temperature, indicated that all plant lines examined yielded statistically identical parameters (Table 9). A similar situation was observed when plants were maintained under non-permissive temperatures (32–34° C., day and night), in that values for net photosynthesis and dark respiration were equivalent among plant lines 277, 2–72 and 306. However, the data presented in Table 9 show that the absolute rates of photosynthesis and dark respiration were considerably higher in the plants exposed to 32–34° C. conditions. These control studies established that neither photosynthetic production nor local consumption differences could provide a basis to explain the MP-induced changes in carbon metabolism [Lucas et al. 1993, supra].

Figure 2A:
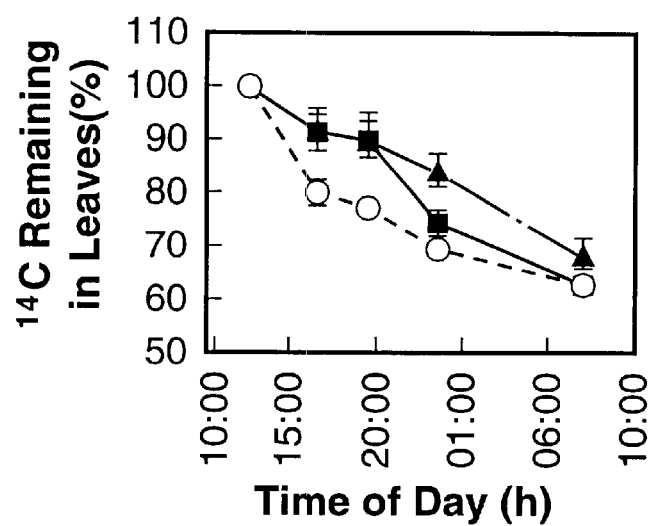
Figure 2B:
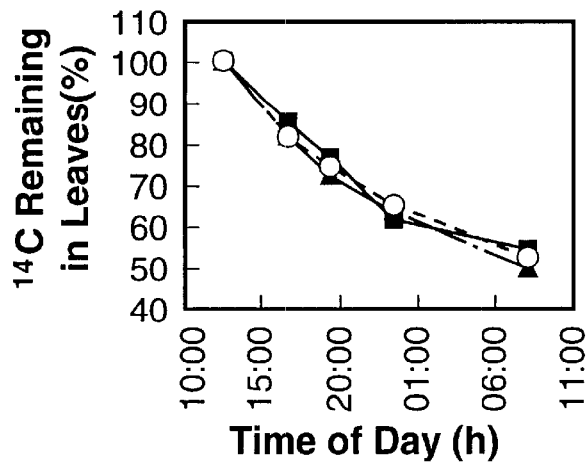
Figure 2C:
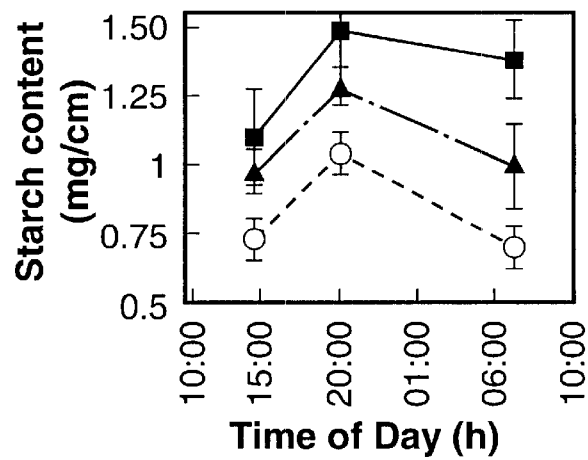
Figure 2D:
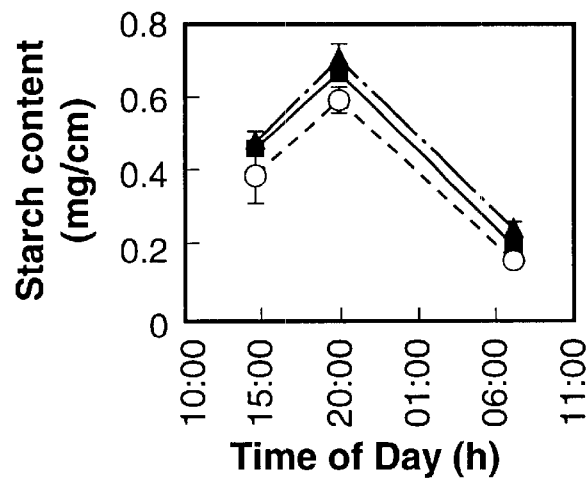
Figure 2E:
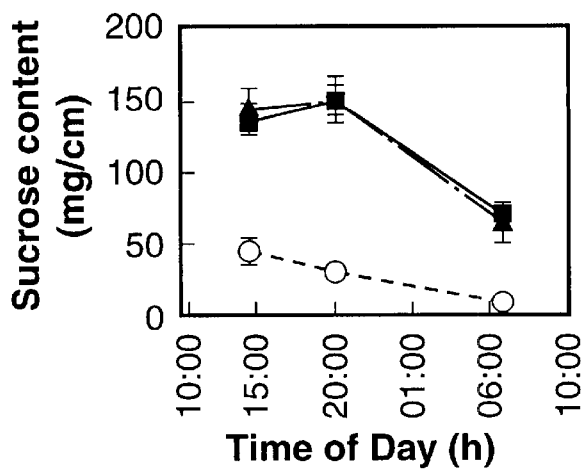
Figure 2F:
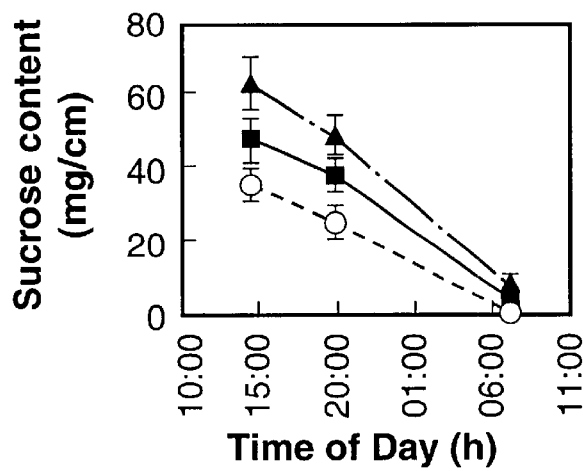
Figure 2G:
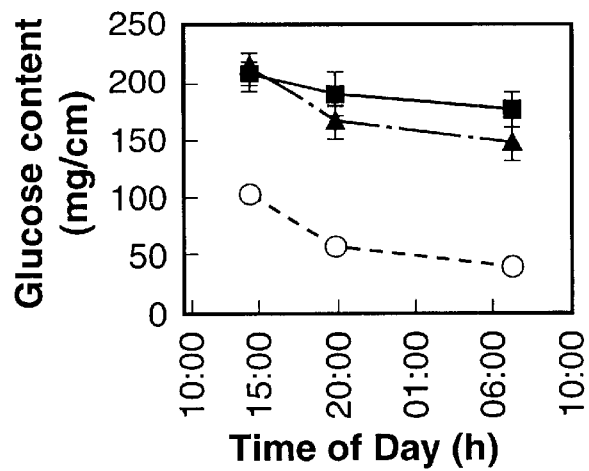
Figure 2H:
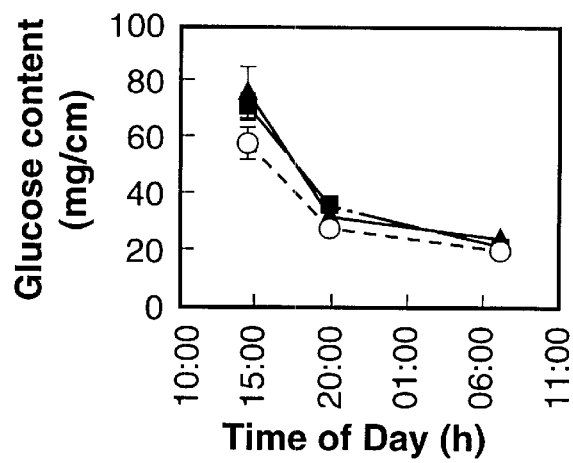
Figure 2I:
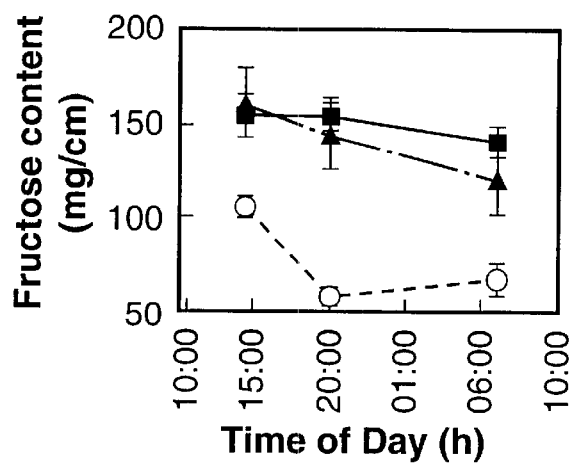
Figure 2J:
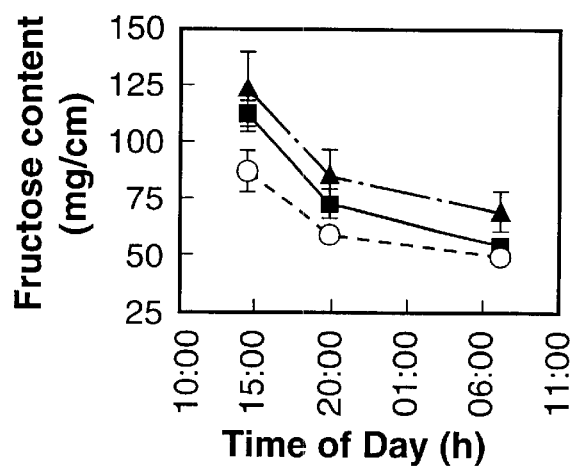

As shown in FIG. 2A, during the first hours after $^{14}$C-labeling, the rate of reduction in radioactivity in source leaves of plants maintained at 25° C. was identical in transgenic plants expressing either the ts mutant or wild-type TMV-MP, but was slower compared to control plants (line 306). Plants were grown in the greenhouse under natural sunlight with a midday average photon flux density of 1500 $\mu$mol.m$^{-2}$.s$^{-1}$, under two temperature regimes of 25°/18° C. day/night (left side) and 34°/32° C. day/night (right side). Radioactivity was detected using a "Rotem" $\beta$ counter (FIGS. 2A & 2B) and leaf discs were analyzed for starch (FIGS. 2C & 2D), sucrose (FIGS. 2E & 2F), glucose (FIGS. 2G & 2H) and fructose (FIGS. 2I & 2J). Five plants from each line and for each temperature regime were used in these experiments, and values represent mean±SE. Interestingly, during the night, the rate of reduction in radioactivity within these source leaves was slower in the ts mutant TMV-MP transgenic plants compared to wild-type TMV-MP transgenic plants. Transgenic plants expressing either the ts mutant or the wild-type TMV-MP were also found to have similar sugar levels when the experiments were performed at 25° C. (FIGS. 2E, 2G & 2I). Consistent with previous findings [Lucas et al. 1993, supra], these sugar levels were always significantly higher in the TMV-MP plants compared with control plants. Interestingly, the starch levels in line 2–72 were intermediate between lines 277 and 306 (FIG. 2C).

Pretreatment of the three plant lines at non-permissive temperatures (32–34° C.) for 72 h caused an increase in the overall rate of reduction of $^{14}$C remaining in the source leaves of all plants tested (cf FIGS. 2A & B). The interesting point to note in these experiments is that the rate of $^{14}$C reduction in source leaves of plant lines 2–72 and 277 increased to such an extent that their values converged with those obtained on control plants (FIG. 2B). Under elevated temperatures, carbohydrate levels declined significantly in all plant lines, and as with $^{14}$C-carbon export, the actual diurnal change in the levels of the individual sugars and starch was similar between the three plant lines (FIGS. 2D, 2F, 2H & 2J). However, sucrose, glucose and fructose levels still exhibited significant differences between lines 2–72, 277 and the control line 306.

A mutant form of the TMV-MP, in which the C-terminal 10 amino acids were deleted, retained full wild-type function, supporting viral infection and causing an increase in plasmodesmal SEL [Berna et al. 1991, supra; Gafny et al. 1992, supra]. Experiments performed on tobacco plants expressing this mutant form of the TMV-MP provided unequivocal support for the hypothesis that this viral protein functions in a pleiotropic manner in transgenic tobacco plants. As shown in Table 10, deletion of the terminal 10 amino acids appeared to eliminate the influence of the TMV-MP on carbohydrate metabolism within mature source leaves. Comparable levels of sucrose, glucose and fructose were detected in plant lines MP1 and 306, while, as expected, plant line 277 (expressing the wild-type TMV-MP gene) had elevated sugar levels. A similar situation was observed with respect to starch metabolism, with plant lines MP1 and 306 having near equivalent values for accumulation and hydrolysis over the experimental period (Table 10). It should be noted that, in plant line 277, the level of starch was higher than in either MP1 or 306 plants and that, in contrast to these plants, little hydrolysis occurred during the night (see also FIG. 2C where a similar situation is reported).

Again, to guard against the effects of positional insertion, somoclonal variation, etc., a second experiment was performed with a different, independent, transgenic tobacco line expressing a TMV-MP in which the C-terminal 10 amino acids were deleted (plant line MP1-1). For this experiment, the influence of the TMV-MP on sugar metabolism in plant line 2004 and 277 (compared with their respective control lines 3001 and 306) was also examined. As illustrated in Table 11, carbohydrate levels in transgenic tobacco plants expressing the C-terminal 10 amino acid deletion form of the TMV-MP were again remarkably similar to the values measured on the relevant control line. Note that these similarities held over the early afternoon, evening and morning periods. Data obtained on plant lines 2004 and 3001 further confirmed that the elevated sugar and starch levels in TMV-MP transgenic plants can be attributed to the presence of the TMV-MP, rather than being due to unrelated events associated with plant transformation.

In this study, the influence of the TMV-MP on carbon metabolism and photosynthate export within source leaves of transgenic tobacco plants is further characterized. Earlier studies showed significantly higher levels of carbohydrates in mature source leaves of TMV-MP transgenic plants compared to control plants [Lucas et al. 1993, supra]. $^{14}CO^2$-labeling experiments were aimed at determining whether the reason for this high accumulation of sugars and starch was due to an alteration in export of newly fixed carbon from the source leaves of TMV-MP expressing plants. The results indicate that during the photoperiod, fully-expanded source leaves of plant lines 277 and 2004 exported $^{14}C$ at a lower rate than equivalently-aged control leaves (FIGS. 1A, B). In addition, preliminary experiments performed on transgenic tobacco plants expressing both the TMV-MP and the TMV-coat protein yielded identical results, in that export was reduced during the day in the presence of the TMV-MP, but not in the presence of the TMV-coat protein.

Given that the sucrose levels are significantly different between TMV-MP expressing plants (lines 277, 2–72 and 2004) and control plants (lines 306 and 3001), it is possible that the differences in $^{14}C$ export could be accounted for in terms of differences in sucrose specific activity. The data presented in Table 8 were used to calculate the rate of $^{14}C$-sucrose exported from the leaf. For these calculations it was assumed that, during the first hours after $^{14}C$-labeling, all reductions in $^{14}C$-sucrose were due to export via the phloem. It was also assumed that within the mature tobacco leaf sucrose is present in one pool in which newly synthesized $^{14}C$-sucrose was able to mix with unlabeled sucrose. Based on these assumptions, the calculated values for $^{14}C$-sucrose export from plant lines 277 and 306 were 13.6 and 15.3 $\mu g$ cm$^{-2}$ h$^{-1}$, respectively. It should be noted that the rate of reduction in the level of radioactivity in the liquid residue fraction (Table 8) was much greater in plant line 306 as compared with plant line 277, which suggests that the differences in $^{14}C$-export between the two lines would actually have been larger than reflected by the above values. Furthermore, parallel measurements of photosynthesis and respiration established that these processes were occurring at equivalent rates in plant lines 277 and 306 (Table 9). Hence, the TMV-MP-induced alteration in $^{14}C$ turnover cannot be due to fundamental changes in either of these processes.

Experiments performed on young, expanding source leaves (leaf #2), in which the TMV-MP has yet to influence either plasmodesmal SEL [Deom et al. 1990, supra] or sugar levels [Lucas et al. 1993, supra] established that the presence of the TMV-MP also resulted in a small, but statistically significant, reduction in $^{14}C$ export in plant line 277 compared to control line 306. As the levels of sucrose would have been similar in these young leaves from lines 277 and 306 [Lucas et al. 1993, supra], the observed reduction in $^{14}C$-export from 277 compared with 306 plants could not have been due to differences in the specific activity of $^{14}C$-sucrose. These results are consistent with earlier studies performed on a different TMV-MP transgenic plant line (274), in which $^{14}C$-labeling experiments established that, under the influence of the TMV-MP, young expanding source leaves partitioned lower amounts of $^{14}C$-photosynthate to the lower stem and root tissues, compared with control plants [Lucas et al. 1993, supra]. Although the effect of the TMV-MP on export from these leaves is small, the long-term influence of this change in carbon allocation could well result in the observed phenotype of a reduced root-to-shoot ratio in TMV-MP-expressing, compared to control tobacco plants [Lucas et al. 1993, supra].

Sucrose is the major translocated sugar in many plant species, including tobacco [Giaquinta 1983, supra]. As demonstrated by analysis of the data presented in Table 8, the actual turnover of $^{14}C$ in the sucrose pool is retarded by the presence of the TMV-MP. Similar trends were also detected for $^{14}C$-glucose and $^{14}C$-fructose, in that the absolute levels of these sugars were higher and the radiolabel was retained in TMV-MP transgenic, compared with control, plants (see also Table 10 and FIG. 2). Given that sucrose is confined mainly to the cytoplasm in wild-type tobacco mesophyll cells [Heineke, D., Wildenberger, K., Sonnewald, U., Willmitzer, L., Heldt, H. W. (1994) Accumulation of hexoses in leaf vacuoles: Studies with transgenic tobacco plants expressing yeast-derived invertase in the cytosol, vacuole or apoplasm. *Planta* 194, 29–41], the TMV-MP may interact at any of the regulatory sites involved in controlling the compartmentation and/or the loading of sucrose into the sieve element-companion cell complex. Reduction in phloem loading would result in a rise in cytosolic sucrose which would lead to an increase in the level of fructose-6-phosphate. This change may then lead to an inhibition of triose phosphate export from the chloroplast which would result in increased partitioning of photosynthate into starch [Stitt, M., Quick, W. P. (1989) Photosynthetic carbon partitioning: its regulation and possibilities for manipulation. *Physiol. Plant.* 77, 633–641]. Although this hypothesis can account for some of the observed effects of the TMV-MP on carbon metabolism and export, as will be pointed out below, the TMV-MP appears to act at additional target sites within the source leaf.

The influence of the TMV-MP on carbon metabolism and export in transgenic tobacco plants was further probed using a ts mutant form of the TMV-MP. The similarity in the results obtained on plant lines 2–72 and 277 (FIG. 2E, G and I), under permissive temperatures, provides further support for the hypothesis that the observed changes in carbon metabolism are caused by the presence of the TMV-MP. Under permissive temperatures (25° C.), $^{14}C$-export during the photoperiod was identical in plant lines 2–72 and 277 (FIG. 2A). Interestingly, in plants expressing the ts form of the TMV-MP gene, the level of starch was intermediate between the levels detected in lines 277 and 306 (FIG. 2C). However, under permissive temperatures, the ts and wild-type TMV-MPs elicited similar effects on sugar accumulation (FIG. 2E, G & I).

Under nonpermissive temperatures (32–34° C.), the ts TMV-MP has no effect on plasmodesmal SEL [Wolf et al. 1991, supra]. Hence, if the influence of the TMV-MP on carbon metabolism were associated with an increase in plasmodesmal SEL, this effect should be negated in plants exposed to a 32–34° C. regime. That this was not the case is established by the data presented in FIG. 2. For example, the level to which sucrose accumulated in the afternoon in plant line 2–72 was twice that measured in plant line 306 (FIG. 2F). The level in plant line 277 was intermediate between 2–72 and 306, which is of interest, as in these plants the plasmodesmata would have remained dilated by the TMV-MP (see also Table 8). Thus, the influence of the ts TMV-MP on sucrose levels strongly supports the hypothesis that the TMV-MP is pleiotropic in its effects within transgenic tobacco plants; i.e., this viral protein contains domains that allow it to interact with secondary plasmodesmata to potentiate the cell-to-cell transport of viral RNA [Lucas and Gilbertson 1994, supra; Waigmann et al. 1994, supra], as well as at least one domain that interferes with an endogenous process involved in regulating photoassimilate storage, translocation and partitioning [Huber, S. C, Huber, J. A. L., McMichael Jr., R. W. (1992) The regulation of sucrose synthesis in leaves. In *Carbon partitioning within and between organisms* (eds. Pollock, C. J., Farrar, J. F., Gordon, A. J.) pp. 1–26. BIOS Scientific Publishers, Ltd., Oxford]. Further evidence in support of the pleiotropic nature of the TMV-MP was provided by the finding that, under nonpermissive temperatures, the levels of glucose and fructose were always highest in plant line 2–72 compared with 277 and 306 (FIGS. 2H & J).

Carbohydrate studies performed on transgenic tobacco plants expressing a mutant form of the TMV-MP gene, in which the C-terminal 10 amino acids were deleted, provided strong additional support for the hypothesis that the TMV-MP has pleiotropic effects in source tobacco leaves. Although removal of this C-terminal region of the TMV-MP has no effect on its viral-related functions [Berna et al. 1991, supra; Gafny et al. 1992, supra], expression of this mutant form in tobacco plants (line MP1 and MP1-1) resulted in a return to normal photosynthetic carbon metabolism (Tables 9 & 10). Since the SEL of mesophyll secondary plasmodesmata, in these transgenic tobacco plants, would still be elevated to values greater than 9.4-kDa [Berna et al. 1991, supra], the results presented in Tables 9 and 10 clearly demonstrate that the TMV-MP has a second property (function), beyond that associated with dilating plasmodesmata, that allows it to interact with cellular processes involved in carbon metabolism and/or export (FIG. 3). In FIG. 3, T→ indicates control sites where the effect of the TMV-MP is overridden when sink strength is altered by raising the growth temperature from 24° to 32° C.; PD, plasmodesmata; SEL, size exclusion limit.

Under the nonpermissive temperature regime used in the ts TMV-MP mutant studies, all plant lines tested behaved in an identical manner, in terms of net $^{14}$C-export and starch metabolism (FIGS. 2B & D). This result suggests that the interaction of the TMV-MP on the regulatory pathway(s) of photosynthate compartmentation and/or export is highly complex. By treating plants at high temperatures we clearly induced a change in the source/sink balance. Under these elevated temperatures the vegetative apex entered into a phase of accelerated development, as evidenced by a striking increase in growth rate of all plant lines tested (data not shown). As expected, high temperatures also caused a significant increase in dark respiration (Table 9). These temperature-induced changes in the apical tissues reflect a substantial increase in overall sink strength, which resulted in enhanced sucrose transport from the source leaves, thereby reducing carbohydrate levels in the mesophyll (FIG. 2). Thus, the temperature-induced convergence of net carbon export from lines 2–72, 277 and 306 (see FIG. 2B) may reflect the influence of an hierarchical control site, involving a feedback (or feedforward) mechanism whose input signal can override some of the sites where the TMV-MP interacts with the endogenous regulatory pathway(s) that controls photosynthate export and partitioning (see FIG. 3).

In this regard it is interesting to note that, under the high temperature regime, the levels of starch were almost identical within the mature source leaves of plant lines 2–72, 277 and 306. Thus, increased sink demand for photosynthate can completely override the effects of the TMV-MP on altered starch metabolism. However, as the levels of sucrose, glucose and fructose remained elevated in the ts TMV-MP plants (line 2–72), it may well be that there are numerous sites at which the TMV-MP can influence (alter) carbon metabolism.

Example 3

It is well established that control over developmental process in plants and animals is orchestrated, at the cellular level, by transcription factors, one class of which is called homeodomain proteins [Gehring W J. (1987) Homeo boxes in the study of development. *Science* 236, 1245–1252; Desplan C., Theis J., O'Farrell P. H. (1988) The sequence specificity of homeodomain-DNA interactions. *Cell* 54, 1081–1090]. In *Zea mays*, Knotted encodes a homeodomain protein which is expressed at very low levels in leaves [Vollbrecht E., Kerstetter R., Lowe B., Veit B., Hake S. (1991) The developmental gene Knotted-1 is a member of a maize homeobox gene family. *Nature* 350, 241–243; Smith L., Greene B., Veit B., Hake S. (1992) A dominant mutation in the maize homeobox gene, Knotted-1, causes its ectopic expression in leaf cells with altered fates. *Development* 116, 21–30], but at high levels in the meristem and ground tissue of unexpanded stems [Vollbrecht et al. 1991, supra; Jackson D., Veit B., Hake S. (1994) Expression of maize KNOTTED1 related homeobox genes in the shoot apical meristem predicts patterns of morphogenesis in the vegetative shoot. *Development* 120, 405–413]. It has also been established that ectopic expression of Knotted in young leaves allows cells that would normally be determinate in nature to undergo continued cell division, resulting in aberrant morphology [Hake S., Freeling M. (1986) Analysis of genetic mosaics shows that the extra epidermal cell divisions in Knotted mutant maize plants are induced by adjacent mesophyll cells. *Nature* 320, 621–623; Smith et al. 1992, supra).

In the normal situation, as well as in tissues where Knotted is expressed ectopically, it appears that the mRNA for Knotted is synthesized in one tissue while the protein, KNOTTED, is detected within the nuclei of cells located within the surrounding tissue(s) [Jackson et al. 1994, supra]. This observation is consistent with the hypothesis that plasmodesmal transport of transcription factors plays a central role in the orchestration of plant development. In Table 12experimental evidence is presented that establishes the validity of this concept. Here, wild-type protein of KNOTTED (KN1) was fluorescently labelled and then microinjected into target cells within intact plants. As with earlier studies on viral movement proteins [Lucas and Gilbertson 1994, supra], evidence was obtained consistent with KN1 having the capacity to interact with plasmodesmata to mediate in its own cell-to-cell transport. Although some mutant forms of KNOTTED could still move out of the target cell into the surrounding tissues, one mutant, KN1 M11Y51, was fully defective in transport function (Table 12). This mutant serves the essential function of an internal control for these experiments.

Having established that KN1 has the ability to mediate in its own cell-to-cell transport, whether KN1 has the ability to interact with its own mRNA to allow the mRNA to undergo transport from the site of synthesis to the cells where KN1 controls tissue development was next tested. As illustrated in Table 13, coinjection of KN1 and fluorescently labelled Knotted mRNA resulted in the efficient transport of mRNA from the target cell into the cells of the surrounding tissues. As expected, injection of fluorescently labelled Knotted mRNA alone resulted in the confinement of the fluorescent probe to the injected cell (Table 13). Further, coinjection of the nonfunctional KN1 M11Y51 mutant and fluorescently labelled Knotted mRNA also resulted in the mRNA being confined to the target cell (Table 13). Collectively, these results provide incontrovertible proof that KN1, a plant-encoded protein, engages in its own cell-to-cell transport as well as the transport of its mRNA. As KNOTTED is a member of a large gene family [Vollbrecht E., Kerstetter R., Lowe B., Veit B., Hake S. (1993) Homeobox genes in plant development: Mutational and molecular analysis. In: *Evolutionary Conservation of Developmental Mechanisms* (ed. A. C. Spradling) pp. 111–123, New York, Wiley-Liss; Jackson et al. 1994, supra], it is highly likely that this ability for macromolecular transport, via plasmodesmata, is central to the control over developmental processes. Identical results have also been obtained with the transcription factors encoded by the MADS box genes deficiens and globosa of Antirrhinum. Microinjection studies clearly established that both of these transcription factors have the capacity to interact with the supramolecular complex of the plasmodesmata to mediate in their cell-to-cell transport.

Example 4

Morphological features as well as biomass partitioning vary as a function of the environmental conditions under which control, wild-type and deletion mutant forms of the TMV-MP transgenic plants are grown [Lucas et al. 1993 supra; Balachandran S., Hull R. J., Vaadia, Y., Wolf S., Lucas, W. J. (1995). Alteration in carbon partitioning, induced by the movement protein of tobacco mosaic virus, originates from the mesophyll and is independent of change in plasmodesmal size exclusion limit. *Plant, Cell & Environment*, 1301-10]. In general these TMV-MP expressing transgenic tobacco plants exhibit varying degrees of reduction in both plant height and root biomass. Growth characteristics for control, wild-type TMV-MP and an N-terminal deletion mutant (Mn-5) are presented in Table 14. Plant line Mn-5 (expressing a mutant TMV-MP in which 3 amino acids [#3–#5] from the N terminal were deleted [Lapidot et al. 1993 supra].) exhibited the most striking phenotype when grown under high light conditions. Plant height as well as total dry weight were approx. 40 and 50 percent lower than those of plant lines 277 (wild type) and 306 (control), respectively. Interestingly, mean internodal length was not significantly different between the three plant lines. It is important to note that the root-to-shoot ratio of plant line Mn-5 was similar to that of plant line 277 despite its specific phenotype. Finally, plants expressing either wild-type or an N-terminal deletion TMV-MP always had lower root-to-shoot ratios compared to control plants (Tables 2 and 14).

Under limiting light conditions, TMV-MP transgenic and vector control plants undergo a significant reduction in root-to-shoot ratio (Table 14). The important point to note is that under these light conditions all plant lines tested had equivalent root-to-shoot ratios, i.e. in the presence of limiting light, the endogenous control system(s) involved in biomass partitioning appears to override the influence of the TMV-MP. However, the presence of the TMV-MP still appeared to influence other developmental processes. For example, while control plants responded to low light conditions by increasing the mean internodal length, which gave rise to an elongation of the stem, a differential growth response was observed in plants expressing the TMV-MP. Mean internodal length increase significantly in plant line 277, but without a concomitant increase in plant height, due to a decrease in the number of nodes produced. Deletion of 3 amino acids within the N-terminus of the TMV-MP (plant line Mn-5) resulted in a complete lack of a response to the low light conditions. Both the number of internodes and the mean internodal length were similar under either 1200 or 150 $\mu$mol m$^{-2}$ s$^{-1}$ of irradiance (Table 14) This differential response to low light conditions, observed with wild-type and N-terminal deletion mutant TMV-MP, suggests that the TMV-MP may interact (interfere) with elements of a phytochrome signal transduction cascade.

Example 5

Cell fate in higher plants is determined by position, rather than by lineage [F. Huala, I. M. Sussex, *Plant Cell* 5, 1157 (1993); I. M. Sussex, *Cell* 56, 225 (1989)] Although environmental and hormonal signals could act in a cell autonomous manner to control cell fate, clonal analysis of developmental mutants has indicated that cell-to-cell transport may be involved in the orchestration of developmental events [W. J. Lucas. *Curr. Opinion Cell Biol.* 7 (673–680)]. For example, expression of Floricaula (FLO), which affects meristem identity in *Antirrhinum majus* (snapdragon), in only the outer (epidermal) layer (L1) of tie meristem, activates down-stream genes involved in flower development [R. Carpenter, F. S. Coen, Development 121, 19 (1995); S. S. Hantke, R. Carpenter, E. S. Coen, *ibid* 121, 27 (1995)] in adjacent cell layers. Similarly, the genotype of the inner layer (L3) of the tomato floral meristem controls development of the outer layers (L2 and L1) [E. J. Symkowiak, I. M. Sussex, *Plant Cell* 4, 1089 (1992)]. These findings are consistent with the hypothesis that FLO, and the fasciated gene product of tomato, potentiate cellular interactions between the three layers of the floral meristem. Such control may involve the selective cell-to-cell transport of proteins through plasmodesmata.

An analysis of movement of the protein and RNA encoded by the maize knotted1 (kn1) homeobox gene [S. Hake, M. Freeling, *Nature* 320, 621 (1986) N. Sinha, S. Hake, *Dev. Biol.* 141, 203 (1990); E. Vollbrecht, B. Veit, N. Sinha, S. Hake, *Nature* 350, 241 (1991); L. G. Smith, B. Green, B. Veit, S. Hake, *Development* 116, 21 (1992)] is here reported. Ectopic expression of kn1 in the vascular tissue of developing maize leaves alters cell differentiation within adjacent mesophyll and epidermal layers, suggesting that a signal moves from one cell layer to another. In situ and immunolocalization studies of the maize shoot apical meristem demonstrated that kn1 mRNA was detected only within the interior (L2) cells of the meristem, whereas KN1 was detected in the L2 cells and in the epidermal (L1) layer [D. Jackson, B. Veit, S. Hake, *Development* 120 405 (1994)].

Serial sections of a maize vegetative shoot apex, processed for in situ hybridization for kn1 mRNA and immunolocalization of KN1, revealed the presence of KN1 in L1 cells in which its mRNA was not detected. The shoot apical meristem was flanked by leaf primordia and older expanding leaves in which kn1 mRNA and KN1 were not detected. Regions in the shoot apical meristem that lacked KN1 predicted the position of leaf primordial development. KN1 was present in a few cells across the base of each developing leaf, These results suggested that, despite the fact that KN1 is a nuclear-localized transcription factor, it is likely the signal that is transported from L2 into the L1 layer, as well as between cell layers in knotted leaves.

In situ hybridization and immunolocalization experiments were performed on paraffin-embedded maize seedling apices. In situ hybridization was performed exactly as described by D. Jackson, B. Veit and S. Hake in *Development* 120, 405 (1994), while for immunolocalization the method of L. G. Smith, B. Greene, B. Veit and S. Hake in *Development* 116, 21 (1992) was used except that tissue was embedded in paraffin wax and sections were predigested with proteinase K (Sigma), at 100 μg/ml in PBS, for 10 min at room temperature and then rinsed twice in PBS before the blocking step. Goat anti-rabbit-alkaline phosphatase )Boehringer Mannheim) was used as the secondary antibody (1:600 dilution) and visualized according to Jackson et al. [D. Jackson, B. Veit, S. Hake. *Development* 120, 405 (1994)]. Sections were lightly counterstained in basic fuchsin (0.005% w/v).

In another study, fluorescently-labeled *Escherichia coli*-expressed KN1 (FITC-KN1) was microinjected into the cytoplasm of plant cells. Wild-type and mutant KN1 were expressed, extracted and labeled with fluorescein isothiocyanate (FITC) using our procedures developed for viral movement proteins [T. Fujiwara, D. Giesman-Cookmeyer, B. Ding, S. A. Lommel, W. J. Lucas, *Plant Cell* 5, 1783 (1993); A. O. Noueiry, W. J. Lucas, R. I. Gilbertson, *Cell* 76, 925 (1994); E. Waigmann, W. J. Lucas, V. Citovsky, P. Zambryski, *Proc. Natl. Acad. Sci.* (USA) 91, 1433 (1994); B. Ding, L. Qiubo, L. Nguyen, P. Palukaitis, W. J. Lucas, *Virology* 207, 345 (1995)]. As an internal control proteins were extracted and FITC-labeled from an *E. coli* preparation which did not contain the kn1 cDNA. Alanine scanning mutants were created in groups of charged amino acids, which are likely to be present in surface domains (PC gene software Intelligenetics). The kn1 cDNA (BamHl-NcoI partial digest) from pKOC10 was inserted into the pET23-d(+) vector (Novagen) to create pDJX-1 Single-stranded virions were produced in the CJ236 (dut ung) strain of *E. coli*, and site-directed mutagenesis was performed using oligonucleotides of 33–48 bases and T7 DNA polymerase according to the manufactor's instructions (United States Biochemical), Mutagenized clones were confirmed by sequencing before transfer to strain BL21 (DE3) for protein production. Microinjections were carried out essentially as previously described [S. Wolf, C. M. Deom, R. N. Beachy, W. J. Lucas, *Science* 246, 377 (1999)], except for the modifications noted in the above citations to procedures developed for viral movement proteins.

The small size of cells in the maize shoot apical meristem precluded us from performing microinjection experiments on such tissues. Instead using developing maize leaves, microinjections were made into mesophyll cells connected to the vascular bundle, as this was the site where ectopically expressed kn1 was shown to alter cell fate. [S. Hake, M. Freeling, *Nature* 320, 621 (1986); N. Sinha, S. Hake, *Dev. Biol.* 141, 203 (1990); E. Vollbrecht B. Veit, N. Sinha, S. Hake, V. *Nature* 350, 241 (1991); L. G. Smith, B. Greene, B. Veit, S. Hake, *Development* 116, 21 (1992)]. FITC-KN1 injected into the cytoplasm of these mesophyll cells moved into bundle sheath and surrounding mesophyll cells (Table 15). Thus, KN1 must be capable of interacting with plasmodesmata to potentiate its own movement from cell to cell.

Tobacco offers another system in which to study KN1, as ectopic meristems are also obtained when KN1 is overexpressed in tobacco [N. Sinha, R. Williams, S. Hake, *Genes & Dev.* 7, 787 (1993)]. FITC-KN1 microinjected into mesophyll cells of tobacco (*Nicotiana tabacum* cv. Samsun) leaves also moved to neighboring cells. See Table 16. Just as an increase in plasmodesmal size exclusion limit (SEL) is required for cell-to-cell transport of viral movement proteins. [W. J. Lucas, R. L. Gilbertson, *Annu. Rev. Phytopath* 32, 387 (1994); T. Fujiwara, D. Giesman-Cookmeyer, B. Ding, S. A. Lommel, W. J. Lucas, *Plant Cell* 5, 1783 (1993); A. O. Noueiry, W. J. Lucas, R. I. Gilbertson, *Cell* 76, 925 (1994); F. Waigmann, W. J. Lucas, V. Citovsky, P. Zambryski, *Proc. Natl. Acad, Sci.* (USA) 91, 1433 (1994); B. Ding; L. Qiubo, L. Nguyen, P. Palukaitis, W. J. Lucas, *Virology* 207, 345 (1995)], an increase in plasmodesmal SEL is also associated with KN1 cell-to-cell movement in maize and tobacco (Tables 15 and 16).

In an experiment focusing on cell-to-cell transports of FITC-labeled KN1 and its effect on plasmodesmal SEL in tobacco mesophyll cells, KN1 and its mutant derivative, M6 (see FIG. 4), were expressed in *E. coli* and extracted proteins were labeled with FITC prior to being used in microinjection studies Immediately after being introduced into a tobacco mesophyll cell FITC-labeled KN1 moved into surrounding cells as indicated by false-color imaging obtained with a Hamamatsu model C1966 analytical system. Containment of FITC-labeled M6 was observed 15 minutes after injection into the cell. Injected 20 kDa FITC-dextran remained indefinitely (60 minutes after injection) within the target cell. Coinjection of 20 kDa FITC-dextran and unlabeled KN1 resulted in extensive movement after 2 minutes after injection.

Cell-to-cell movement of injected Lucifer yellow CH (MW 457), a membrane-impermeant fluorescent probe, established that plasmodesmata in the injected tissues displayed normal characteristics [A. W. Robards, W. J. Lucas, *Annu. Rev. Plant Physiol. Plant Molec. Biol.* 41, 369 (1990)] (Tables 15 and 16). Furthermore, the lack of movement of FITC-labeled bacterial proteins established that KN1 movement was not an artifact of the preparative techniques employed (Table 16).

Microinjection of 9.4 or 20 kDa FITC-dextran alone did not result in movement out of the injected cell, but coinjection of these FITC-dextrans with unlabeled KN1 gave rise to the same spread of fluorescence as detected when FITC-KN1 was introduced into the cell (Tables 15 and 16). This KN1-induced increase in plasmodesmal SEL also permitted the cell-to-cell movement of a labeled, coinjected, 20 kDa soybean cytosolic protein, soybean trypsin inhibitor (Table 16). Occasionally, KN1 permitted the movement of a 39 kDa FITC-dextran and so the upper plasmodesmal SEL associated with KN1 transport is greater than 20 and close to 39 kDa.

Protein domains essential for KN1 cell-to-cell movement were investigated using a series of alanine scanning mutants (created as described above). (FIG. 4). Of the 9 mutants studied, only one (M6) showed a significant reduction in ability to move from cell to cell (Table 16). The M6 mutation resides in a potential nuclear localization sequence present in the N-terminal region of the homeodomain [E. Vollbrecht, R. Kerstetter, B. Lowe, B. Veit, S. Hake, in *Evolutionary Conservation of Developmental Mechanisms*, A. C. Spalding, Ed. (Wiley-Liss, New York, 1993) 111; R. Kerstetter, E. Vollbrecht, B. Lowe, B. Veit, J. Yamaguchi, S. Hake, *Plant Cell* 6, 1877 (1994); C. Lincoln, J. Long, J. Yamaguchi, K. Serikawa, S. Hake, *Plant Cell* 6, 1859 (1994)] Whether this reflects homology between nuclear and plasmodesmal transport systems must await the identification and characterization of other transcriptional regulators that also have the capacity for plasmodesmal transport.

Although the other mutants of KN1 retained the capacity to dilate plasmodesmata and potentiate their own cell-to-cell transport (Table 16), the rate and extent of movement of each mutant KN1 was reduced compared to wild-type KN1 FITC-KN1 was routinely detected in neighhoring cells one to two seconds after its injection into a mesophyll cell, with further movement through five to ten surrounding cells in approx. 30 seconds. Although the period before each mutant FITC-KN1 could be detected in the neighboring cells was also short (a few seconds), subsequent movement into the second layer of cells required from 3 to 5 minutes. Furthermore, rarely was fluorescence detected beyond this second layer of mesophyll cells. Analysis of plant viral movement proteins (by procedures described and cited above), on the other hand, showed that alanine scanning mutants either exhibited normal movement, or were incapable (0% movement) of cell-to-cell transport. The varied response of KN1 mutants may reflect the presence of multiple domains involved in mediating efficient plasmodesmal transport or interaction with the plasmodesmata.

Having established that KN1 interacts with plasmodesmata to increase SEL and mediate in its own cell-to-cell transport, characteristics held in common with many viral movement proteins, it was next investigated whether KN1 could also mediate trafficking of nucleic acids, although the results above suggest no such ability. Sense kn1 RNA was TOTO-labeled and coinjected into mesophyll cells with unlabeled KN1. Kn1 sense or antisense RNA was transcribed using T3 or T7 RNA polymerase from linearized pKOC10 plasmid which contained the full length cDNA. The DNA template was digested with RQ1 DNase (Promega) and the RNA was phenol extracted and ethanol precipitated. Kn1 RNA (1.6 kb) was resuspended in 20 μl DEPC-$H_2O$ and concentration and purity was determined by spectroscopy. Sense and antisense RNA (500 μg/ml) were labeled with the nucleotide-specific fluorescent probe, TOTO-1 (Molecular Probes), as previously described. All kn1 RNA-TOTO preparations were adjusted to 225 μg/ml for use in microinjection experiments. CMV RNA-TOTO was adjusted to 250–500 μg/ml.

In the presence of KN1, the fluorescence associated with kn1 sense RNA-TOTO moved as rapidly and extensively from cell-to-cell as did FITC-KN1 when it alone was injected into this tissue. Control microinjection experiments, involving kn1 sense RNA-TOTO alone, kn1 antisense RNA-TOTO alone; or unlabeled KN1 plus kn1 antisense RNA-TOTO, established the specificity of KN1-mediated kn1 RNA transport, as in each of these cases, the fluorescent probes remained in the injected cell (Table 17). The M6 mutant of KN1, which was least able to transport itself, did not potentiate the cell-to-cell transport of kn1 sense RNA-TOTO (Table 17).

Coinjection of KN1 and kn1 sense RNA-TOTO revealed movement of the kn1 sense RNA-TOTO into tobacco mesophyll cells within the vicinity of the injected cell after 1 minute. Kn1 antisense RNA-TOTO failed to move out of the target cell when coinjected with KN1. At 15 minutes after coinjection, a false-color image showed that fluorescence had accumulated in what appeared to be the nucleus. A tobacco mesophyll cell coinjected with KN1 and CMV RNA-TOTO after 15 minutes showed fluorescence remains confined to the injected cell. Purified CMV RNA was prepared [P. Paukaitis, M. Zaitlin. *Virology* 132, 426 (1984)] and TOTO-labeled as described by Ding et al. This preparation contained 3 single-stranded RNA species, RNA1 (3.3 kb), RNA2 (3.0 kb) and RNA3 (2.2 kb). The procedures of Ding et al. were used to prepare and FITC-label the CMV 3*a* movement protein. Although KN1 would presumably have trafficked into surrounding cells, it failed to transport the CMV RNA-TOTO. Coinjection of CMV 3*a* movement protein and kn1 sense RNA-TOTO into a tobacco mesophyll cell resulted in extended CMV 3*a* movement protein-mediated transport of the kn1 sense RNA-TOTO into the surrounding cells, 2 minutes after injection.

KN1 was selective in terms of the RNA that it would traffic as shown by coinjection of TOTO-labeled cucumber mosaic virus (CMV) single-stranded sense RNA and KN1 (Table 17). The CMV movement protein in contrast potentiated cell-to-cell transport both of its own RNA and of kn1 RNA (Table 17), consistent with the known non-specificity of viral movement proteins.

Our finding that KN1 has the capacity to move from cell to cell provides a plausible explanation for the non-cell autonomy of the dominant KN1 mutation, as well as the lack of autonomy found with other developmental mutations [P. W. Becraft, M. Freeling, *Genetics* 136, 295 (1994)].

These studies on KN1 provide important insights into the molecular events that orchestrate developmental processes in plants and establish a conceptual basis for explaining the plasticity of cell fate in the plant meristem.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

Each and every reference cited herein is, in its entirety, expressly incorporated by reference into the forgoing disclosure.

TABLE 1

Description of TMV-MP and various mutant forms of the TMV-MP used to examine the influence of the MP on carbon allocation in transgenic tobacco plants expressing these genes.

| Transgenic line | Type of MP gene expressed | Reference[a] |
| --- | --- | --- |
| 277 | TMV-MP (wild-type) (*N. tabacum* Xanthi nn) | Deom et al. (1987) |
| 306 | Vector control, (plasmid without MP; Xanthi nn) | Deom et al. (1987) |
| MN-1 | 33 amino acid deletion in the C-terminus of TMV-MP, (Xanthi NN) | Berna et al. (1991); Gafny et al. (1992) |
| MN-2 | 55 amino acid deletion in the C-terminus of TMV-MP, (Xanthi NN) | Berna et al. (1991); Gafny et al. (1992) |

TABLE 1-continued

Description of TMV-MP and various mutant forms of the TMV-MP used to examine the influence of the MP on carbon allocation in transgenic tobacco plants expressing these genes.

| Transgenic line | Type of MP gene expressed | Reference[a] |
|---|---|---|
| Mn-1 | 10 amino acid deletion in the C-terminus of TMV-MP, (Xanthi nn) | Verna et al. (1991); Gafny et al. (1992) |
| Mn-2 | 10 amino acid deletion in the C-terminus of TMV-MP, (Xanthi nn) | Verna et al. (1991); Gafny et al. (1992) |
| Mn-3 | 73 amino acid deletion in the C-terminus of TMV-MP, (Xanthi nn) | Berna et al. (1991); Gafny et al. (1992) |
| Mn-4 | 116 amino acid deletion in the C-terminus of TMV-MP, (Xanthi nn) | Lapidot et al. (1993) |
| Mn-5 | 3–5 amino acid deletion in the N-terminus of TMV-MP, (Xanthi nn) | Lapidot et al. (1993) |
| Mn-6 | Same as Mn-5, (no protein detected even though MP was present) | Berna et al. (1991); Gafny et al. (1992) |
| 3001 | Vector control, (plasmid without MP, Xanthi NN) | Deom et al. (1991) |
| 2005 | TMV-MP, (Xanthi NN) | Deom et al. (1991) |
| RMN-1 | TMV-MP expressed in phloem and hair tip cells, (under rolC promoter in Xanthi NN) | Reimann-Philipp & Beachy (1993) |
| RMn-1 | TMV-MP expressed in phloem and hair tip cells, (under rolC promoter in Xanthi nn) | Reimann-Philipp & Beachy (1993) |
| RGN-1 | Vector control, (plasmid without MP expressed in phloem and hair tip cells (under rolC promoter in Xanthi NN)) | Reimann-Philipp & Beachy (1993) |

[a]See primary reference for details relating to plasmid construction and plant transformation.

TABLE 2

Root-to-shoot ratios obtained from experiments performed on grafted transgenic tobacco plants expressing either the TMV-MP (line 227) or the vector control (plasmid only; line 306).

| Scion/stock | R/S[a] |
|---|---|
| 277/306 | 0.07 ± 0.008[b,c] |
| 306/277 | 0.12 ± 0.001[b,d] |
| 277/277 | 0.06 ± 0.005[c] |
| 306/306 | 0.10 ± 0.007[d] |

[a]Root-to-shoot ratios expressed as a fraction of the root biomass divided by total above-ground plant material. Values represnet mean ± SE (n = 3–8).
[b]significantly different at $P < 0.01$;
[c,d]not significantly different at $P = 0.05$

TABLE 3

Biomass partitioning in transgenic tobacco lines in which the TMV-MP was expressed in different plant tissues. (Data represent one of two sets of identical, indepently run experiments. Values are mean ± SE, n = 5–10.)

| Trangenic line | Total plant weight | Dry weight (g)[a] | | | |
|---|---|---|---|---|---|
| | | Leaves | Stems | Roots | R/S |
| 306 | 26.4 ± 2.9[a,b] | 12.5 ± 1.4[c] | 11.8 ± 1.3[f,g] | 2.1 ± 0.3[h,i] | 0.09 ± 0.004[j,k] |
| 277 | 20.7 ± 1.5[a,c,d] | 12.2 ± 1.1[e] | 7.4 ± 0.5[f] | 1.0 ± 0.1[h] | 0.05 ± 0.001[j] |
| RMn-1 | 28.4 ± 2.6[b,c] | 13.1 ± 0.8[e] | 12.7 ± 1.3 | 2.6 ± 0.2[i] | 0.10 ± 0.005[k] |
| RGN-1 | 23.7 ± 1.5[b,d] | 12.3 ± 0.5[e] | 9.5 ± 0.6 | 1.9 ± 0.1[i] | 0.09 ± 0.002[k] |
| RMN | 21.9 ± 2.0[b,d] | 11.0 ± 1.1[e] | 9.9 ± 0.9[g] | 2.0 ± 0.2[i] | 0.10 ± 0.002[k] |

[a]Plants were 50 days old at time of harvest. Values represent mean ± SE, n = 6.
[b]significantly different at $P < 0.01$,
[c]not significantly different at $P = 0.05$.

TABLE 4

Biomass partitioning in transgenic tobacco lines expressing different deletion mutant forms of the TMV-MP. Data represent one of two sets of identical, independently run experiments.

| Transgenic line | Total plant weight | Dry weight (g)[a] | | | |
|---|---|---|---|---|---|
| | | Leaves | Stems | Roots | R/S |
| Xanthi NN 301 | 2.5 ± 2.2 | 10.5 ± 0.9 | 10.2 ± 1.1[g] | 1.9 ± 0.2 | 0.09 ± 0.004[b,d] |
| 2005 | 17.6 ± 1.6 | 11.8 ± 0.9 | 5.3 ± 0.7 | 0.6 ± 0.1 | 0.03 ± 0.004[b,f] |
| MN-1 | 14.8 ± 1.2 | 9.2 ± 0.9 | 5.1 ± 0.5 | 0.6 ± 0.1 | 0.04 ± 0.004[f] |
| MN-2 | 19.1 ± 2.1 | 10.0 ± 0.7 | 8.1 ± 1.3[g] | 1.0 ± 0.2 | 0.05 ± 0.008[f] |
| Xanthi nn 306 | 26.4 ± 2.9 | 12.5 ± 1.4 | 11.8 ± 1.3 | 2.1 ± 0.3 | 0.09 ± 0.004[c,d] |
| 277 | 20.7 ± 1.5 | 12.2 ± 1.1[j] | 7.4 ± 0.5[h] | 1.0 ± 0.1[i] | 0.05 ± 0.001[c,e] |
| Mn-3 | 18.5 ± 1.8 | 9.1 ± 0.5 | 8.4 ± 0.6 | 1.0 ± 0.1 | 0.06 ± 0.008[e] |
| Mn-4 | 21.9 ± 0.8 | 10.4 ± 2.2 | 10.4 ± 0.4 | 1.3 ± 0.4 | 0.06 ± 0.006[e] |
| Mn-5 | 10.3 ± 2.7 | 5.8 ± 1,3[j] | 3.8 ± 1.0[h] | 0.6 ± 0.1[i] | 0.07 ± 0.003[e] |
| Mn-6 | 25.2 ± 0.4 | 11.3 ± 0.2 | 11.9 ± 0.5 | 2.0 ± 0.2 | 0.09 ± 0.003[d] |

[a]Plants were 70–75 days old at time of harvest. Values represent mean ± SE, n = 5–10.
[b,c,g]significantly different at $P < 0.01$;
[h,i,j]significantly different at $P < 0.05$;
[d,e,f]not significantly different at $P = 0.05$.

TABLE 5

Growth characteristics of transgenic tobacco plants expressing different deletion mutant forms of the TMV-MP. Data represent one to two sets of identical, independently run experiments.

| Transgenic line | Growth charcteristics[a] | |
|---|---|---|
| | Plant height (cm) | Number of leaves |
| Xanthi NN | | |
| 3001 | 41 ± 1.5[b,f] | 18 ± 0.5[i] |
| 2005 | 27 ± 1.5[b,c] | 18 ± 0.5[i] |
| MN-1 | 27 ± 1.7[c] | 17 ± 0.6[1] |
| MN-2 | 37 ± 1.1[f] | 20 ± 0.4[i] |
| Xanthi nn | | |
| 306 | 46 ± 0.9[d,e] | 19 ± 1.1[g,h,i] |
| 277 | 29 ± 1.1[c,d] | 17 ± 0.7[i] |
| Mn-3 | 33 ± 1.5[c] | 16 ± 1.8[g] |
| Mn-4 | 33 ± 0.5[c] | 16 ± 0.6[i] |
| Mn-5 | 26 ± 2.8[c] | 15 ± 1.1[h] |
| Mn-6 | 47 ± 1.6[e] | 19 ± 0.4[i] |

[a]Plants were 70–75 days old at time of harvest. Values represent mean ± SE, n = 5–10.
[b,d,f,g,h]significantly different at $P < 0.05$;
[c,e,i]not significantly differnt at $P = 0.05$.

TABLE 6

Biomass partitioning in transgenic tobacco lines infected with tobacco mosaic virus (strain PV230). Plants were inoculated with TMV when they had six fully developed leaves, and were harvested at 24 days post-inoculation at which time they were 60 days old. (Values represent mean ± SE, n = 4.)

| Transgenic line | Total plant weight | Dry weight (g) | | | |
|---|---|---|---|---|---|
| | | Leaves | Stems | Roots | R/S |
| 306 unifected | 45.6 ± 3.1 | 21.5 ± 1.0 | 19.5 ± 2.1 | 4.7 ± 0.3 | 0.11 ± 0.004[a] |
| infected | 40.3 ± 1.0 | 18.6 ± 0.4 | 19.1 ± 1.2 | 2.5 ± 0.1 | 0.07 ± 0.003[a,b] |

TABLE 6-continued

Biomass partitioning in transgenic tobacco lines infected with tobacco mosaic virus (strain PV230). Plants were inoculated with TMV when they had six fully developed leaves, and were harvested at 24 days post-inoculation at which time they were 60 days old. (Values represent mean ± SE, n = 4.)

| Transgenic line | | Total plant weight | Dry weight (g) | | | |
|---|---|---|---|---|---|---|
| | | | Leaves | Stems | Roots | R/S |
| 277 | unifected | 31.8 ± 1.0 | 17.0 ± 0.8 | 12.7 ± 0.5 | 2.1 ± 0.2 | 0.07 ± 0.005[b] |
| | infected | 34.7 ± 1.5 | 18.3 ± 0.7 | 14.0 ± 0.9 | 2.3 ± 0.2 | 0.07 ± 0.003[b] |

[a]significantly different at $P < 0.01$,
[b]not significantly different at $P = 0.05$

TABLE 7

Biomass partitioning in transgenic tobacco lines (Mn-1 and Mn-2) expressing the TMV-MP in which 10 amino acids were deleted from the C-terminus. (Note that Mn-1 and Mn-2 represent two independent transformed lines.)

| Transgenic line | Total plant weight | Dry weight (g) | | | |
|---|---|---|---|---|---|
| | | Leaves | Stems | Roots | R/S |
| 306 | 26.2 ± 2.4 | 12.2 ± 0.7 | 11.4 ± 0.8 | 2.6 ± 0.1 | 0.11 ± 0.007[b,c] |
| 277 | 19.3 ± 2.0 | 11.4 ± 0.7 | 6.7 ± 0.9 | 1.2 ± 0.1 | 0.07 ± 0.008[b] |
| Mn-1 | 26.4 ± 2.0 | 12.3 ± 0.7 | 11.7 ± 0.9 | 2.4 ± 0.2 | 0.10 ± 0.006[c] |
| Mn-2 | 27.1 ± 2.8 | 12.5 ± 0.7 | 11.8 ± 0.6 | 2.8 ± 0.3 | 0.12 ± 0.001[c] |

[a]Plants were 50 days old at time of harvest. Values represent mean ± SE, n = 6.
[b]significantly different at $P < 0.01$,
[c]not significantly different at $P = 0.05$.

TABLE 8

$^{14}$C-carbohydrates and total carbohydrate content within leaves of TMV-MP transgenic (line 277) and vector control (line 306) tobacco plants. Plants were grown in a greenhouse under natural sunlight with average midday photon flux density of 1500 $\mu mol \cdot m^{-2} \cdot s^{-1}$. Six plants were used from each line. Leaf disks were punched from fully expanded leaves (leaf #5–6), and were analyzed for radioactivity and carbohydrate content (values in parentheses) of each compound.

| Plant line | Time of day | Radioactivity[a] and content | | | | | | |
|---|---|---|---|---|---|---|---|---|
| | | SC[b] | GL | FR | STR | LR | SR | TOT |
| 306 | 10:30 | 368 (28.7) | 161 (38.0) | 138 (54.2) | 506 (462) | 533 | 123 | 1829 |
| | 14:00 | 120 (37.7) | 158 (43.7) | 183 (54.3) | 546 (577) | 319 | 133 | 1459 |
| | 17:30 | 81 (31.5) | 117 (36.4) | 136 (52.5) | 505 (659) | 255 | 152 | 1244 |
| Significance[c] | | * * | ns ns | ns ns | ns * | * | * | * |
| 277 | 10:30 | 479 (47.6) | 176 (92.4) | 148 (114.5) | 631 (1002) | 564 | 128 | 2127 |
| | 14:00 | 293 (61.4) | 171 (101.6) | 173 (125.8) | 579 (1041) | 535 | 151 | 1902 |
| | 17:30 | 227 (59.0) | 168 (95.4) | 185 (118.5) | 573 (1076) | 519 | 169 | 1841 |
| Significance[b] | | * * | ns ns | ns ns | ns ns | ns | * | * |

[a]Radioactivity and content (values in parenthesis) presented as DPM and $\mu g \cdot cm^{-2}$, respectively.
[b]SC, sucrose; GL, glucose; FR, fructose; STR, starch; LR, liquid residue; SR, solid residue; TOT, total radioactivity
[c]* and ns represent significant and not significantly different, respectively, at $P = 0.05$.

TABLE 9

Temperature effects on photosynthesis and dark respiration in wild-type TMV-MP transgenic (line 277), ts mutant TMV-MP transgenic (line 2-72) and control (line 306) tobacco plants. Mature leaves (leaf #56 on 12 to 14-leaf plants) were measured using a closed infrared gas-exchange system. (Six plants of each line were used per experiment and value presented represent mean ± SE.)

| Plant line | Temperature (° C.) | Plasmodesmal[a] SEL (kDa) | $\mu$mol $CO_2 \cdot m^{-2} \cdot s^{-1}$ | |
|---|---|---|---|---|
| | | | Photosynthesis | Dark respiration |
| 306 | 25 | 0.8 | 14.4 ± 0.9 | 2.6 ± 0.2 |
| 277 | 25 | >9.4 | 12.5 ± 1.0 | 2.4 ± 0.2 |
| 2-72 | 25 | >9.4 | 14.1 ± 3.3 | 2.2 ± 0.2 |
| 306 | 32–34 | 0.8 | 23.8 ± 1.3 | 6.1 ± 0.4 |
| 277 | 32–34 | >9.4 | 24.6 ± 0.2 | 5.9 ± 0.4 |
| 2-72 | 32–34 | 0.8 | 22.3 ± 0.9 | 6.2 ± 0.7 |

[a]Data from Wolf et al. (1991)

TABLE 10

Carbohydrate content within source leaves of transgenic tobacco plants expressing wild-type TMV-MP (line 277), a 10 amino acid C-terminal deletion mutant of the TMV-MP (line MP1), and the vector control (line 306). Experimental details as in Table 8 (mean ± SE, n = 5).

| Time of day | Plant line | Sucrose[a] | Glucose | Fructose | Starch[b] |
|---|---|---|---|---|---|
| 13:00 | 277 | 125.6 ± 12.7 d | 236.7 ± 46.4 d | 172.5 ± 33.6 | 817 ± 51 d |
| | MP1 | 61.7 ± 16.8 e | 143.3 ± 26.8 e | 126.5 ± 23.7 | 521 ± 40 e |
| | 306 | 65.7 ± 11.5 e | 129.4 ± 12.9 e | 130.4 ± 12.9 | 528 ± 54 e |
| Significance[c] | | ** | * | ns | ** |
| 19:00 | 277 | 177.1 ± 8.7 d | 194.3 ± 45.9 d | 162.6 ± 36.2 d | 979 ± 146 |
| | MP1 | 61.9 ± 14.4 f | 105.1 ± 20.5 e | 102.5 ± 15.6 e | 854 ± 103 |
| | 306 | 115.9 ± 7.3 e | 106.9 ± 14.6 e | 126.3 ± 14.5 de | 758 ± 74 |
| Significance | | ** | * | * | ns |
| 07:00 | 277 | 52.5 ± 9.3 d | 169.9 ± 37.4 d | 129.4 ± 21.4 d | 954 ± 151 d |
| | MP1 | 5.5 ± 4.3 e | 64.7 ± 7.8 e | 72.3 ± 13.5 e | 445 ± 72 e |
| | 306 | 11.2 ± 5.0 e | 59.8 ± 10.0 e | 92.4 ± 14.0 de | 304 ± 33 c |
| Significance | | ** | ** | * | ** |

[a]Sugars presented as $\mu g \cdot cm^{-2}$
[b]Starch content presented as $\mu g$ glucose equivalents $\cdot cm^{-2}$
[c]*, **, and ns represent significant (P = 0.05 and P = 0.01) and not significantly different, respectively (d, e, f indicate significant differences between values, using the Student-Newman-Keuls multiple range test; ns, no significant difference).

TABLE 11

Carbohyrate content within source leaves of transgenic tobacco plants expressing wild-type TMV-MP (lines 277, 2004), a 10 amino acid C-terminal deletion mutant of the TMV-MP (second, independent transformant, line MP1-1), and the vector controls (lines 306 and 3001). Experimental details as in Table 8 (mean ± SE, n = 5).

| Time of day | Plant line | Sucrose[a] | Glucose | Fructose | Starch[b] |
|---|---|---|---|---|---|
| 13:00 | 277 | 194.6 ± 23.7 d | 311.1 ± 24.7 d | 182.0 ± 18.0 | 1129 ± 98 d |
| | MP1-1 | 106.9 ± 11.6 c | 175.4 ± 25.2 c | 143.8 ± 16.9 | 500 ± 15 c |
| | 306 | 112.1 ± 20.0 c | 173.4 ± 32.9 c | 143.9 ± 23.5 | 588 ± 80 c |

TABLE 11-continued

Carbohyrate content within source leaves of transgenic tobacco plants expressing wild-type TMV-MP (lines 277, 2004), a 10 amino acid C-terminal deletion mutant of the TMV-MP (second, independent transformant, line MP1-1), and the vector controls (lines 306 and 3001). Experimental details as in Table 8 (mean ± SE, n = 5).

| Time of day | Plant line | Sucrose[a] | Glucose | Fructose | Starch[b] |
|---|---|---|---|---|---|
| Significance[c] | | ** | ** | ns | ** |
| | 2004 | 158.1 ± 20.9 f | 317.9 ± 25.3 f | 182.5 ± 32.1 f | 956 ± 141 f |
| | 3001 | 62.1 ± 8.9 g | 69.5 ± 16.7 g | 75.3 ± 16.5 g | 301 ± 29 g |
| Significance | | ** | ** | ** | ** |
| 19:00 | 277 | 208.2 ± 21.0 d | 277.8 ± 21.3 d | 165.3 ± 14.3 d | 1438 ± 146 d |
| | MP1-1 | 99.3 ± 7.1 e | 128.7 ± 12.6 c | 104.7 ± 6.9 e | 584 ± 103 e |
| | 306 | 119.7 ± 21.7 e | 146.3 ± 28.8 e | 111.7 ± 16.8 e | 822 ± 123 c |
| Significance | | ** | ** | * | ** |
| | 2004 | 187.3 ± 19.6 f | 271.7 ± 11.0 f | 150.2 ± 15.8 f | 1091 ± 59 f |
| | 3001 | 64.8 ± 3.8 g | 54.2 ± 8.2 g | 74.0 ± 7.2 g | 396 ± 39 g |
| Significance | | ** | ** | ** | ** |
| 07:00 | 277 | 140.3 ± 13.4 d | 286.1 ± 13.5 d | 172.2 ± 15.6 d | 1048 ± 89 d |
| | MP1-1 | 46.0 ± 6.0 e | 86.7 ± 19.0 e | 96.2 ± 11.7 e | 424 ± 66 e |
| | 306 | 49.3 ± 8.5 e | 92.0 ± 24.4 e | 98.8 ± 15.2 e | 488 ± 135 e |
| Significance | | ** | ** | ** | ** |
| | 2004 | 110.6 ± 18.2 f | 247.5 ± 31.2 f | 154.8 ± 21.9 f | 1132 ± 129 f |
| | 3001 | 38.6 ± 1.2 g | 54.3 ± 19.2 g | 54.4 ± 6.2 g | 189 ± 41 g |
| Significance | | ** | ** | ** | ** |

[a]Sugars presented as $\mu g \cdot cm^{-2}$
[b]Starch content presented as $\mu g$ glucose equivalents $\cdot cm^{-2}$
[c]*, **, and ns represent significant (P = 0.05 and P = 0.01) and not significantly different, respectively (d, e, f, g indicate significant differences between values, using the Student-Newman-Keuls multiple range test).

TABLE 12

KN1 Capacity to Interact with Plasmodesmata Explored Using Mutational Analysis.

| KN1 | Microinjections[a] | Movement[b] |
|---|---|---|
| KN1 | | |
| wild-type | 11 (14) | + |
| KN1 mutants: | | |
| M2Y39 | 8 (11) | + |
| M9Y12 | 9 (9) | + |
| M11Y51 | 3 (40) | − |

[a]Number of injections in which KN1 protein moved from target cell into surrounding tissue (total number of injections in each experiment given in parenthesis).
[b]Movement of fluorescently labeled KN1 protein was detected using a fluorescence microscope and permanent images of were recorded on videotape. + = movement out of the target cell; − = no movement out of injected target cell.

TABLE 13

KN1 has the Ability to Interact with its own mRNA and Traffic it through Plasmodesmata.

| Injected material Movement[b] | Microinjections [a] |
|---|---|
| Knotted-1 mRNA | 0 (15) − |
| Knotted-1 mRNA plus KN1 | 11 (15) + |
| Knotted-1 mRNA plus mutant KN1 M11Y51 | 0 (10) − |

[a]Number of injections in Knotted-1 mRNA moved from target cell into surrounding tissue (total number of injections in each experiment given in parenthesis)

[b]Movement of fluorescently labeled Knotted-1 mRNA was detected using a fluorescence microscope and permanent images of were recorded on videotape. + = movement out of the target cell; − = no movement out of injected target cell.

TABLE 14

Growth characteristics and biomass partitioning in vector control tobacco plants (306) versus those in transgenic lines expressing the wild type (277) and N-terminal deletion mutant form (Mn-5) of the TMV-MP grown under low and high light levels.

| Growth light intensity[1] ($\mu$mol m$^{-2}$ s$^{-1}$) | Transgenic line | Plant height (cm) | Number of leaves | Mean internodal length (cm) | Dry weight (g) | | | |
|---|---|---|---|---|---|---|---|---|
| | | | | | Leaves | Stems | Root | R/S |
| 1200 | 306 | 107 ± 7 | 28 ± 2.0 | 3.8 | 13.2 ± 0.8 | 10.6 ± 0.5 | 3.7 ± 0.5 | 0.16 ± 0.006 |
| | 277 | 89 ± 5 | 26 ± 1.4 | 3.4 | 11.4 ± 0.4 | 7.4 ± 0.8 | 2.0 ± 0.3 | 0.11 ± 0.009 |
| | Mn-5 | 56 ± 4 | 17 ± 1.5 | 3.3 | 7.0 ± 0.6 | 4.2 ± 0.3 | 1.2 ± 0.1 | 0.11 ± 0.006 |
| 150 | 306 | 124 ± 4 | 22 ± 0.8 | 5.6 | 9.6 ± 0.8 | 8.1 ± 0.7 | 1.1 ± 0.2 | 0.06 ± 0.009 |
| | 277 | 94 ± 6 | 17 ± 1.5 | 5.5 | 5.6 ± 0.8 | 4.5 ± 0.8 | 0.6 ± 0.08 | 0.06 ± 0.007 |
| | Mn-5 | 56 ± 7 | 15 ± 1.5 | 3.7 | 3.3 ± 0.5 | 1.8 ± 0.4 | 0.3 ± 0.06 | 0.06 ± 0.006 |

[1]Plants were grown in a greenhouse and the light intensity was adjusted using shade cloth. Measurements of the spectral distribution under the two light regimes indicated that only the actual intensity was altered. Photoperiod was approx. 14 h day/10 h night.

TABLE 15

A maize homeodomain protein, KN1, interacts with plasmodesmata to increase size exclusion limit of maize mesophyll cells[a] potentiates its own cell-to-cell transport.

| Injected materail | Microinjections (n) | Movement (%)[b] |
|---|---|---|
| Lucifer yellow CH | 12 | 11 (92) |
| FITC-KN1 | 12 | 10 (82) |
| 9.4 kDa FITC-dextran | 12 | 1 (8) |
| KN1 + 9.4 kDa FITC-dextran | 11 | 9 (82) |

[a]The normal SEL of plasmodesmata in such plant sells is 800–1000 Da (5). The largest material known to pass through mesophyll plasmodesmata is a viral movement protein of 35 kDa (6). Developing maize leaves (one to two cm in width) from young seedlings (14 days postgermination) were used n these experiments.
[b]Number of injections in which the fluorescently labeles probe moved from the injected cell into surrounding tissue. (n) total number of injections in wach experiment. Fluorescence was detected using a Leitz Orthoplan epi-illumination microscope coupled with a Hamamatsu model C1966-20 analytical system, and permanent images were recorded on videotape.

TABLE 16

KN1 interacts with plasmodesmata to increase size exclusion limit of tobacco mesophyll cells and potentiates its own cell-to-cell transport.

| Injected material | Microinjections (n) | Movement (%)[a] |
|---|---|---|
| Lucifer yellow CH | 54 | 49 (91) |
| FITC-KN1 | 33 | 29 (88) |
| FITC-labeled bacterial proteins | 10 | 0 (0) |
| 9.4 kDa FITC-dextran | 35 | 3 (9) |
| KN1 + 9.4 kDa FITC-dextran | 38 | 29 (76) |
| 20 kDa FITC-dextran | 11 | 1 (9) |
| KN1 + 20 kDa FITC-dextran | 19 | 16 (84) |
| KN1 + 39 kDa FITC-dextran | 25 | 5 (20) |
| 20 kDa FITC-soybean trypsin inhibitor | 15 | 2 (13) |
| KN1 + 20 Kda FITC-soybean trypsin inhibitor | 10 | 10 (100) |
| FITC-KN1 (M6)[b] | 15 | 1 (7) |
| KN1 (M6) + 9.4 kDa FITC-dextran | 16 | 3 (19) |
| KN1 (M1) + 9.4 kDa FITC-dextran | 11 | 8 (73) |
| KN1 (M2) + 9.4 kDa FITC-dextran | 8 | 6 (75) |
| KN1 (M3) + 9.4 kDa FITC-dextran | 8 | 6 (75) |
| KN1 (M4) + 9.4 kDa FITC-dextran | 12 | 8 (75) |
| KN1 (M5) + 9.4 kDa FITC-dextran | 9 | 9 (100) |
| KN1 (M7) + 9.4 kDa FITC-dextran | 7 | 6 (86) |
| KN1 (M8) + 9.4 kDa FITC-dextran | 8 | 6 (75) |
| KN1 (M9) + 9.4 kDa FITC-dextran | 16 | 10 (63) |

[a]Number of injections in which the fluorescently labeled probe moved from the injected cell into surrounding tissue. (n) total number of injections in each experiment. Movement of fluorescently labeld kn1 mRNA, or CMV RNA, was detected as described in Table 1.
[b]Details on the amino acid changes engineered for each KN1 mutant are given in FIG. 4.

TABLE 17

KN1 can selectively traffic its own mRNA through plasmodesmata.

| Injected material | Microinjections (n) | Movement (%)[a] |
|---|---|---|
| kn1 sense RNA-TOTO | 25 | 1 (4) |
| kn1 sense RNA-TOTO plus KN1 | 22 | 20 (91) |
| kn1 sense RNA-TOTO plus KN1 M6 | 10 | 0 (0) |
| kn1 antisense RNA-TOTO | 10 | 2 (20) |
| kn1 antisense RNA-TOTO plus KN1 | 10 | 0 (0) |
| CMV RNA-TOTO plus CMV 3a MP | 15 | 13 (87) |
| CMV RNA-TOTO plus KN1 | 15 | 3 (20) |
| kn1 sense RNA-TOTO plus CMV 3a MP | 15 | 12 (80) |

[a]Number of injections in which kn1 mRNA, or CMV RNA, moved from target cell into surrounding tissue. (n) number of injections in each experiment. Movement of fluorescently labeled kn1 mRNA, or CMV RNA, was detected as described in Table 15.

I claim:

1. A method for altering biomass partitioning in a plant, comprising:

operably linking a promoter that is active in a plant to a modified nucleic acid encoding a tobamovirus 30 kDa movement protein mutated in the SEL domain to produce a vector; and introducing said vector into a plant, wherein the nucleic acid is expressed to produce a tobamovirus 30 kDa movement protein mutated in the SEL domain, wherein said plant's biomass partitioning is altered.

2. The method as recited in claim 1, wherein said modified nucleic acid is a modified Tobacco Mosaic Virus nucleic acid.

3. A method for altering carbon metabolism in a plant, comprising:

operably linking a promoter that is active in a plant to a modified nucleic acid encoding a tobamovirus 30 kDa movement protein mutated in the SEL domain to produce a vector; and introducing said vector into a plant, wherein the nucleic acid is expressed to produce a tobamovirus 30 kDa movement protein mutated in the SEL domain, wherein said plant's carbon metabolism is altered.

4. The method as recited in claim 3, wherein said modified nucleic acid is a modified Tobacco Mosaic Virus nucleic acid.

5. A method for altering the overall height of a plant, comprising:

operably linking a promoter that is active in a plant to a modified nucleic acid encoding a tobamovirus 30 kDa movement protein mutated in the SEL domain to produce a vector; and introducing said vector into a plant, wherein the nucleic acid is expressed to produce a tobamovirus 30 kDa movement protein mutated in the SEL domain, wherein said plant's overall height is altered.

6. The method as recited in claim 5, wherein said modified nucleic acid is a modified Tobacco Mosaic Virus nucleic acid.

7. A method for altering biomass partitioning in a plant, comprising:

expressing a nucleic acid encoding a tobamovirus 30 kDa movement protein in source leaf tissue of a plant, wherein the encoded tobamovirus 30 kDa movement protein is produced, and said plant's biomass partitioning is altered.

8. The method as recited in claim 7, wherein said nucleic acid is a Tobacco Mosaic Virus nucleic acid.

9. A method for altering carbon metabolism in a plant, comprising:

expressing a nucleic acid encoding a tobamovirus 30 kDa movement protein in source leaf tissue of a plant, wherein the encoded tobamovirus 30 kDa movement protein is produced, and said plant's carbon metabolism is altered.

10. The method as recited in claim 9, wherein said nucleic acid is a Tobacco Mosaic Virus nucleic acid.

11. A method for altering plant height, comprising:

expressing a nucleic acid encoding a tobamovirus 30 kDa movement protein in source leaf tissue of a plant, wherein the encoded tobamovirus 30 kDa movement protein is produced, and said plant's height is altered.

12. The method as recited in claim 11, wherein said nucleic acid is a Tobacco Mosaic Virus nucleic acid.

13. A method for altering biomass partitioning in a plant, comprising:

operably linking a promoter that is active in a plant to a modified nucleic acid encoding a tobamovirus 30 kDa movement protein that has an N-terminal deletion of about 3 to 5 amino acids to produce a vector; and introducing said vector into a plant, wherein the nucleic acid is expressed to produce a tobamovirus 30 kDa movement protein comprising an N-terminal deletion, wherein said plant's biomass partitioning is altered.

14. The method as recited in claim 13, wherein said modified nucleic acid is a modified Tobacco Mosaic Virus nucleic acid.

15. A method for altering carbon metabolism in a plant, comprising:

operably linking a promoter that is active in a plant to a modified nucleic acid encoding a tobamovirus 30 kDa movement protein that has an N-terminal deletion of about 3 to 5 amino acids to produce a vector; and introducing said vector into a plant, wherein the nucleic acid is expressed to produce a tobamovirus 30 kDa movement protein comprising an N-terminal deletion, wherein said plant's carbon metabolism is altered.

16. The method as recited in claim 15, wherein said modified nucleic acid is a modified Tobacco Mosaic Virus nucleic acid.

17. A method for altering the overall height of a plant, comprising:

operably linking a promoter that is active in a plant to a modified nucleic acid encoding a tobamovirus 30 kDa movement protein that has an N-terminal deletion of about 3 to 5 amino acids to produce a vector; and introducing said vector into a plant, wherein the nucleic acid is expressed to produce a tobamovirus 30 kDa movement protein comprising an N-terminal deletion, wherein said plant's overall height is altered.

18. The method as recited in claim 17, wherein said modified nucleic acid is a modified Tobacco Mosaic Virus nucleic acid.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 359 amino acids
      (B) TYPE: amino acid
      (D) TOPOLOGY: unknown (ii) MOLECULE TYPE: protein (ix) FEATURE:
      (D) OTHER INFORMATION: nuclear-localized transcription
          factor e ncoded by the maize knotted 1 (kn1)
          homeobox gene (xi) SEQUENCE DESCRIPTION: SEQ ID NO: 1:

```
Met Glu Glu Ile Thr Gln His Phe Gly Val G ly Ala Ser Ser His Gly
                 5                  10                  15

His Gly His Gly Gln His His His His H is His His His Pro Trp
             20                  25                  30

Ala Ser Ser Leu Ser Ala Val Val Ala Pro L eu Pro Pro Gln Pro Pro
             35                  40                  45

Ser Ala Gly Leu Pro Leu Thr Leu Asn Thr V al Ala Ala Thr Gly Asn
         50                  55                  60

Ser Gly Gly Ser Gly Asn Pro Val Leu Gln L eu Ala Asn Gly Gly Gly
 65                  70                  75                  80

Leu Leu Asp Ala Cys Val Lys Ala Lys Glu P ro Ser Ser Ser Ser Pro
                 85                  90                  95

Tyr Ala Gly Asp Val Glu Ala Ile Lys Ala L ys Ile Ile Ser His Pro
                100                 105                 110

His Tyr Tyr Ser Leu Leu Thr Ala Tyr Leu G lu Cys Asn Lys Val Gly
            115                 120                 125

Ala Pro Pro Glu Val Ser Ala Arg Leu Thr G lu Ile Ala Gln Glu
        130                 135                 140

Val Glu Ala Arg Gln Arg Thr Ala Leu Gly G ly Leu Ala Ala Ala Thr
145                 150                 155

Glu Pro Glu Leu Asp Gln Phe Met Glu Ala T yr His Glu Met Leu Val
160                 165                 170                 175

Lys Phe Arg Glu Glu Leu Thr Arg Pro Leu G ln Glu Ala Met Glu Phe
                180                 185                 190

Met Arg Arg Val Glu Ser Gln Leu Asn Ser L eu Ser Ile Ser Gly Arg
                195                 200                 205

Ser Leu Arg Asn Ile Leu Ser Ser Gly Ser S er Glu Glu Asp Gln Glu
            210                 215                 220

Gly Ser Gly Gly Glu Thr Glu Leu Pro Glu V al Asp Ala His Gly Val
225                 230                 235

Asp Gln Glu Leu Lys His His Leu Leu Lys L ys Tyr Ser Gly Tyr Leu
240                 245                 250                 255

Ser Ser Leu Lys Gln Glu Leu Ser Lys Lys L ys Lys Gly Lys Leu
                260                 265                 270

Pro Lys Glu Ala Arg Gln Gln Leu Leu Ser T rp Trp Asp Gln His Tyr
            275                 280                 285
```

-continued

```
Lys Trp Pro Tyr Pro Ser Glu Thr Gln Lys V al Ala Leu Ala Glu Ser
        290             295              300

Thr Gly Leu Asp Leu Lys Gln Ile Asn Asn T rp Phe Ile Asn Gln Arg
        305             310              315

Lys Arg His Trp Lys Pro Ser Glu Glu Met H is His Leu Met Met Asp
320             325             330              335

Gly Tyr His Thr Thr Asn Ala Phe Tyr Met A sp Gly His Phe Ile Asn
            340             345              350

Asp Gly Gly Leu Tyr Arg Leu Gly
            355         359
```